US009085757B2

(12) United States Patent
Firpo et al.

(10) Patent No.: US 9,085,757 B2
(45) Date of Patent: Jul. 21, 2015

(54) PRODUCTION OF INSULIN PRODUCING CELLS

(75) Inventors: Meri Firpo, Minneapolis, MN (US); Zhaohui Geng, New Brighton, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 13/702,031

(22) PCT Filed: Jun. 17, 2011

(86) PCT No.: PCT/US2011/040956
§ 371 (c)(1),
(2), (4) Date: Feb. 13, 2013

(87) PCT Pub. No.: WO2011/160066
PCT Pub. Date: Dec. 22, 2011

(65) Prior Publication Data
US 2013/0243735 A1    Sep. 19, 2013

Related U.S. Application Data

(60) Provisional application No. 61/355,916, filed on Jun. 17, 2010.

(51) Int. Cl.
| | |
|---|---|
| C12N 5/00 | (2006.01) |
| C12N 5/071 | (2010.01) |
| A61K 35/39 | (2015.01) |
| A61K 35/12 | (2015.01) |

(52) U.S. Cl.
CPC ............. *C12N 5/0678* (2013.01); *A61K 35/39* (2013.01); *C12N 5/0676* (2013.01); *A61K 35/12* (2013.01); *C12N 2501/11* (2013.01); *C12N 2501/16* (2013.01); *C12N 2501/19* (2013.01); *C12N 2501/335* (2013.01); *C12N 2501/415* (2013.01); *C12N 2501/91* (2013.01); *C12N 2506/02* (2013.01); *C12N 2506/45* (2013.01)

(58) Field of Classification Search
CPC ............................... A61K 35/12; C12N 5/0676
USPC ....................................................... 435/377
See application file for complete search history.

(56) References Cited

U.S. PATENT DOCUMENTS

2009/0004152 A1    1/2009  Martinson et al.

FOREIGN PATENT DOCUMENTS

| | | |
|---|---|---|
| WO | WO-2007047509 A2 | 4/2007 |
| WO | WO-2011160066 A1 | 12/2011 |

OTHER PUBLICATIONS

Sulzbacher et al. "Activin A-induced differentiation of embryonic stem cells into endoderm and pancreatic progenitors—the influence of differentiation factors and culture conditions", Stem Cell Rev., 2009, 35:159-173.*
"International Application Serial No. PCT/US2011/040956, International Search Report mailed Nov. 23, 2011", 6 pgs.
"International Application Serial No. PCT/US2011/040956, Written Opinion mailed Nov. 23, 2011", 10 pgs.
Jiang, Wei, et al., "In vitro derivation of functional insulin-producing cells from human embryonic stem cells", Cell Res., 17(4), (Apr. 2007), 333-44.
Kroon, Evert, et al., "Pancreatic endoderm derived from human embryonic stem cells generates glucose-responsive insulin-secreting cells in vivo", Nature Biotechnology, 26(4), (Apr. 2008), 443-452.
Matveyenko, A. V, et al., "Inconsistent formation and nonfunction of insulin-positive cells from pancreatic endoderm derived from human embryonic stem cells in athymic nude rats", Am J Physiol Endocrinol Metab., 299(5), (Nov. 2010), E713-20.
Phillips, Blaine W, et al., "Directed differentiation of human embryonic stem cells into the pancreatic endocrine lineage", Stem Cells Dev., 16(4), (Aug. 2007), 561-78.
Rajagopal, J., et al., "Insulin staining of ES cell progeny from insulin uptake", Science, 299(5605), (Jan. 17, 2003), 363.
Shim, J. H, et al., "Directed differentiation of human embryonic stem cells towards a pancreatic cell fate", Diabetologia, 50(6), (Jun. 2007), 1228-38.
Sulzbacher, Sabine, et al., "Activin A-Induced Differentiation of Embryonic Stem Cells into Endoderm and Pancreatic Progenitors—The Influence of Differentiation Factors and Culture Conditions", Stem Cell Reviews and Reports, 5(2), (Jun. 1, 2009), 159-173.
Tateishi, Keisuke, et al., "Generation of insulin-secreting islet-like clusters from human skin fibroblasts", J Biol Chem., 283(46), (Nov. 14, 2008), 31601-7.
Zhang, Donghui, et al., "Generation of pancreatic islet cells from human embryonic stem cells", Sci China C Life Sci., 52(7), (Jul. 2009), 615-21.
"International Application Serial No. PCT/US2011/040956, International Preliminary Report on Patentability mailed Dec. 19, 2012", 9 pgs.

* cited by examiner

*Primary Examiner* — Bin Shen
(74) *Attorney, Agent, or Firm* — Schwegman Lundberg & Woessner, P.A.

(57) ABSTRACT

The invention provides methods for differentiating stem cells along the pancreatic lineage as well as large scale culture methods. The present invention further provides pancreatic progenitor cells derived from stem cells to provide pancreatic cells to a subject.

16 Claims, 23 Drawing Sheets

PRODUCTION OF INSULIN PRODUCING CELLS

RELATED APPLICATION

This application is a U.S. National Stage Filing under 35 U.S.C. 371 from International Application No. PCT/US2011/040956, filed on Jun. 17, 2011, and published as WO 2011/160066 on Dec. 22, 2011, which application/publication claims priority from U.S. Provisional Application Ser. No. 61/335,916, filed Jun. 17, 2010, the contents of which applications and/or publications are incorporated herein by reference in their entirety.

BACKGROUND OF THE INVENTION

Pancreas

The pancreas is an elongated, tapered organ which lies to the rear of the upper left hand side of the abdominal cavity. It has been anatomically described as containing three main sections including a head (widest end—located near the duodenum), a body, and a tail (tapered end—located near the spleen). This organ houses two main tissue types: exocrine tissue, comprised of both acinar and ductal cells; and endocrine tissue, containing cells which produce hormones (i.e., insulin) for delivery into the bloodstream. The exocrine pancreas, comprising about 95% of the pancreatic mass, is an acinar gland containing clusters of pyramidal secretory cells (referred to as acini) that produce digestive enzymes (i.e., amylase, lipase, phospholipase, trypsin, chymotrypsin, aminopeptidase, elastase and various other proteins). These enzymes are delivered to the digestive system by tubes constructed of cuboidal ductal cells, which also produce bicarbonate for digestive purposes. Between the secretory acini and ductal tubes is located a connecting cell component referred to as centroacinar cells.

The endocrine pancreas, comprising only about 1-2% of the pancreatic mass, contains clusters of hormone-producing cells referred to as islets of Langerhans (the islet cells are responsible for the maintenance of blood glucose levels by secreting insulin). These clusters are made up of at least seven cell types, including, but not limited to, insulin-producing β-cells, glucagon-producing α-cells, somatostatin-producing δ-cells, and PP-cells which produce pancreatic polypeptide. In addition, a subpopulation of endocrine cells referred to as ε-cells has been described.

Diabetes

Diabetes mellitus is a medical condition characterized by variable yet persistent high blood-glucose levels (hyperglycemia). Diabetes is a serious devastating illness that is reaching epidemic proportions in both industrialized and developing countries. In 1985, there were approximately 30 million people with diabetes worldwide, which increased 135 million in 1995 and is expected to increase further by close to 50% by 2050. Diabetes is the fifth leading cause of death in the United States. According to the American Diabetes Association, the economic cost of diabetes in the U.S. in 2002 was $132 billion, including $92 billion of direct costs. This figure is expected to reach in excess of $190 billion by 2020.

Generally, diabetes mellitus can be subdivided into two distinct types: Type 1 diabetes and Type 2 diabetes. Type 1 diabetes is characterized by little or no circulating insulin and it most commonly appears in childhood or early adolescence. It is caused by the destruction of the insulin-producing beta cells of the pancreatic islets. To survive, people with Type 1 diabetes must take multiple insulin injections daily and test their blood sugar multiple times per day. However, the multiple daily injections of insulin do not adequately mimic the body's minute-to-minute production of insulin and precise control of glucose metabolism. Blood sugar levels are usually higher than normal, causing complications that include blindness, renal failure, non-healing peripheral vascular ulcers, the premature development of heart disease or stroke, gangrene and amputation, nerve damage, impotence and it decreases the sufferer's overall life expectancy by one to two decades.

Type 2 diabetes usually appears in middle age or later and particularly affects those who are overweight. In Type 2 diabetes, the body's cells that normally require insulin lose their sensitivity and fail to respond to insulin normally. This insulin resistance may be overcome for many years by extra insulin production by the pancreatic beta cells. Eventually, however, the beta cells are gradually exhausted because they have to produce large amounts of excess insulin due to the elevated blood glucose levels. Ultimately, the overworked beta cells die and insulin secretion fails, bringing with it a concomitant rise in blood glucose to sufficient levels that it can only be controlled by exogenous insulin injections. High blood pressure and abnormal cholesterol levels usually accompany Type 2 diabetes. These conditions, together with high blood sugar, increase the risk of heart attack, stroke, and circulatory blockages in the legs leading to amputation.

There is a third type of diabetes in which diabetes is caused by a genetic defect, such as Maturity Onset Diabetes of the Young (MODY). MODY is due to a genetic error in the insulin-producing cells that restricts its ability to process the glucose that enters this cell via a special glucose receptor. Beta cells in patients with MODY cannot produce insulin correctly in response to glucose, resulting in hyperglycemia and require treatment that eventually also requires insulin injections.

The currently available medical treatments for insulin-dependent diabetes are limited to insulin administration, pancreas transplantation (either with whole pancreas or pancreas segments) and pancreatic islet transplantation. Insulin therapy is by far more prevalent than pancreas transplantation and pancreatic islet transplantation. However, controlling blood sugar is not simple. Despite rigorous attention to maintaining a healthy diet, exercise regimen, and always injecting the proper amount of insulin, many other factors can adversely affect a person's blood-sugar control including: stress, hormonal changes, periods of growth, illness or infection and fatigue. People with diabetes must constantly be prepared for life threatening hypoglycemic (low blood sugar) and hyperglycemic (high blood sugar) reactions.

In contrast to insulin administration, whole pancreas transplantation or transplantation of segments of the pancreas is known to have cured diabetes in patients. However, due to the requirement for life-long immunosuppressive therapy, the transplantation is usually performed only when kidney transplantation is required, making pancreas-only transplantations relatively infrequent operations. Although pancreas transplants are very successful in helping people with insulin-dependent diabetes improve their blood sugar to the point they no longer need insulin injections and reduce long-term complications, there are a number of drawbacks to whole pancreas transplants. Most importantly, getting a pancreas transplant involves a major operation and requires the use of life-long immunosuppressant drugs to prevent the body's immune system from destroying the pancreas that is a foreign graft. Without these drugs, the pancreas is destroyed in a matter of days. The risks in taking these immunosuppressive drugs is the increased incidence of infections and tumors that can both be life threatening.

Pancreatic islet transplants are much simpler and safer procedures than whole pancreas transplants and can achieve the same effect by replacing beta cells. However, the shortage of islet cells available for transplantation remains an unsolved problem in islet cell transplantation. Since islets form only about 2% of the entire pancreas, isolating them from the rest of the pancreas that does not produce insulin takes approximately 6 hours. Although an automated isolation method has made it possible to isolate enough islets from one pancreas to transplant into one patient, as opposed to the 5 or 6 organs previously needed to carry out one transplant, the demand for islets still exceeds the currently available supply of organs harvested from cadavers. Additionally, long term resolution of diabetic symptoms is often not achieved.

Stem Cells

Pluripotent stem cells including embryonic stem (ES) cells (Evans and Kaufman (1981); Martin (1981); Thomson et al. (1998)) and induced pluripotent stem (iPS) cells (Takahashi and Yamanaka (2006); Takahashi et al. (2007); Yu et al. (2007)) can be infinitely expanded in vitro and differentiated into any cell type when exposed to the appropriate signals (Keller et al. (2005); Soria et al. (2001); Kumar et al. (2003); Magliocca and Odorico (2006); Madsen (2006)). Previous studies have shown that human ES cells can be directed to differentiate into functional endocrine cells, and that transplantation of these pancreatic-like cells derived from human ES (hES) cells in vitro normalizes glucose levels in diabetic mice (Shim et al. (2007); Jiang et al. (2007); Philips et al. (2007); D'Amour et al. (2005); D'Amour et al. (2005); Kroon et al. (2008)). Induced pluripotent stem cells have been generated from non-diabetic and diabetic donors, and induced to differentiate into pancreatic insulin-producing cells, although no demonstration of function in vivo have been reported (Zhang et al. (2009); Tateishi et al. (2008); Maehra et al. (2009)). Induced pluripotent stem cells have the advantage of being accessible from any individual, and thus, could provide patient-specific donor cell source for a range of diseases. Prior studies of directed differentiation of pluripotent cells to insulin-producing cells required multi-step culture procedures using multiple cytokines.

SUMMARY OF THE INVENTION

Described herein is a differentiation method that provides reproducible patterns of differentiation to pancreatic cells from multiple human ES and iPS lines capable of reversing diabetes in mice using only four added proteins. Additionally, it is demonstrated herein that the suspension differentiation strategy can be scaled from about 1 mL volumes in static culture to about 100 mL and higher volumes (including, but not limited to, about 10 ml, about 20 ml, about 30 ml, about 40 ml, about 50 ml, about 60 ml, about 70 ml, about 80 ml, about 90 ml, about 100 ml, about 150 ml, about 200 ml, about 250 ml, about 300 ml, about 350 ml, about 400 ml, about 450 ml, about 500 ml, about 550 ml, about 600 ml, about 650 ml, about 700 ml, about 750 ml, about 800 ml, about 850 ml, about 900 ml, about 950 ml, about 1 liter, about 1.5 liters, about 2 liters about 2.5 liters, about 3 liters, about 3.5 liters, about 4 liters, about 4.5 liters, about 5 liters, about 5.5 liters, about 6 liters, about 6.5 liters, about 7 liters, about 7.5 liters, about 8 liters, about 8.5 liters, about 9 liters, about 9.5 liters, about 10 liters, about 15 liters, about 20 liters, about 25 liters, about 30 liters, about 35 liters, about 40 liters, about 45 liters, about 50 liters, about 100 liters, about 200 liters, about 300 liters, about 400 liters, about 500 liters and higher) in stirred bioreactors. Thus, the growth of cells in large numbers to facilitate transplantation in large animal and human transplantation has been achieved. The results indicate that the efficiency of iPS cell differentiation into insulin-producing cells was comparable in a stirred suspension bioreactor culture with static culture. The bioreactor allowed the culture of cells at higher densities, without loss of cells or viability. Diabetic mice were rescued by transplantation of iPS-derived cells from 100 ml bioreactor cultures. This is the first demonstration of large-scale culture of pancreatic islet cells suitable for transplantation therapies.

One embodiment provides compositions and methods for providing insulin-expressing cells and progenitors from stem and iPS cells.

One embodiment provides a method to differentiate stem cells to pancreatic progenitor cells comprising the steps of: a) contacting the stem cells with at least one member of the TGFβ family of cytokines and at least one member of the Wnt family of proteins, b) contacting the cells obtained from step a) with at least one member of the TGFβ family of cytokines, at least one member of the Wnt family of proteins, and an agent that inhibits sonic hedgehog activity; and c) contacting the cells obtained from step b) with a member of the Epidermal growth factor (EGF) family of proteins; so as to yield pancreatic progenitor cells. In one embodiment, the at least one member of the TGFβ family of cytokines is activinA or nodal. In another embodiment, the at least one member of the Wnt family is Wnt3 or Wnt3A. In another embodiment, the at least one member of the EGF family is EGF.

Another embodiment provides a method to differentiate stem cells to pancreatic progenitor cells comprising the steps of: a) contacting the iPS cells with Activin A and Wnt3a; b) contacting the cells obtained from step a) with Activin-A, Wnt3a, and an agent that inhibits sonic hedgehog activity; and c) contacting the cells obtained from step b) with EGF; so as to yield pancreatic progenitor cells. One embodiment provides the a method to differentiate stem cells to pancreatic progenitor cells consisting essentially of the steps of: a) contacting the iPS cells with Activin A and Wnt3a; b) contacting the cells obtained from step a) with Activin-A, Wnt3a, and an agent that inhibits sonic hedgehog activity; and c) contacting the cells obtained from step b) with EGF; so as to yield pancreatic progenitor cells.

In one embodiment, the stem cells are embryonic (embryonic stem (ES) cell has unlimited self-renewal and can differentiate into all tissue types; ES cells are derived from the inner cell mass of the blastocyst or primordial germ cells from a post-implantation embryo (embryonic germ cells or EG cells)) or adult stem cells (e.g., MAPCs or MIAMI (marrow-isolated adult multilineage inducible) cells). In another embodiment, the stem cells are induced pluripotent stem (iPS) cells. In one embodiment, the stem cells are mammalian cells, such as human cells.

One embodiment further provides contacting the cells obtained from step c) with at least one member of the TGFβ family of cytokines, betacellulin, exendin4 or a combination thereof to yield cells expressing insulin. In one embodiment, the at least one member of the TGFβ family of cytokines is GDF-11.

One embodiment provides for contacting the cells obtained from step c) with GDF-11, betacellulin, exendin4 or a combination thereof to yield cells expressing insulin. In one embodiment, the cells expressing insulin or having increased expression of insulin secrete insulin, c-peptide or a combination thereof. In one embodiment, the insulin is insulin-1.

In one embodiment, the agent that inhibits sonic hedgehog activity is cyclopamine or an anti-SHH antibody.

In one embodiment, the differentiation of the stem cell occurs in a cell culture dish. In another embodiment, the differentiation of the stem cell occurs in a bioreactor.

One embodiment provides a composition comprising or consisting essentially of Activin-A, Wnt 3a and an agent that inhibits sonic hedgehog activity and stem cells. In one embodiment, the composition comprises the cells prepared by methods described herein and cell culture medium or a pharmaceutically acceptable carrier. One embodiment provides a method to prepare a composition comprising combining cells obtained by the methods described herein of with cell culture medium or a pharmaceutically acceptable carrier.

One embodiment provides a method to provide pancreatic cells to a subject in need thereof comprising: a) contacting the stem cells with at least one member of the TGFβ family of cytokines and at least one member of the Wnt family of proteins, b) contacting the cells obtained from step a) with at least one member of the TGFβ family of cytokines, at least one member of the Wnt family of proteins, and an agent that inhibits sonic hedgehog activity; and c) contacting the cells obtained from step b) with a member of the Epidermal growth factor (EGF) family of proteins; and administering the cells so as to provide pancreatic cells in the subject. In one embodiment, the at least one member of the TGFβ family of cytokines is activinA or nodal. In another embodiment, the at least one member of the Wnt family is Wnt3 or Wnt3A. In another embodiment, the at least one member of the EGF family is EGF.

One embodiment provides a method to provide pancreatic cells to a subject in need thereof comprising: a) contacting stem cells with Activin A and Wnt 3a; b) contacting the cells obtained from step a) with Activin-A, Wnt3a, and an agent that inhibits sonic hedgehog activity; c) contacting the cells obtained from step b) with EGF; and administering the cells so as to provide pancreatic cells in the subject. In one embodiment, the stem cells are embryonic or adult stem cells (e.g., MAPCs). In another embodiment, the stem cells are induced pluripotent stem (iPS) cells.

In one embodiment, the obtained in step c) are contacted with at least one member of the TGFβ family of cytokines, betacellulin, Exendin4 or a combination thereof to yield cells expressing insulin prior to administration to the subject. In one embodiment, the least one member of the TGFβ family of cytokines is GDF-11.

In one embodiment, the cells obtained from step c) are contacted with GDF-11, betacellulin, exendin4 or a combination thereof to yield cells expressing insulin prior to administration to the subject.

Another embodiment provides a method to provide insulin expressing cells to a subject in need thereof comprising: a) contacting stem cells with Activin A and Wnt 3a; b) contacting the cells obtained from step a) with Activin-A, Wnt3a, and an agent that inhibits sonic hedgehog activity; c) contacting the cells obtained from step b) with EGF; d) contacting the cells obtained from step c) with GDF-11, betacellulin, exendin4 or a combination thereof so as to yield cells expressing insulin or having increased expression of insulin; and e) administering the cells expressing insulin or having increased expression of insulin to the subject. In one embodiment, the stem cells are embryonic or adult stem cells (e.g., MAPCs or MIAMI cells). In another embodiment, the stem cells are induced pluripotent stem (iPS) cells.

In one embodiment, the subject is a mammal, such as a human. In one embodiment, the subject has a pancreatic disorder or injury, such as diabetes (e.g., Type I or Type II diabetes), obesity, pancreatic atresia, pancreas inflammation, alpha1-antitrypsin deficiency, hereditary pancreatitis, pancreatic cancer, pancreatic enzyme deficiency, hyperinsulinism, physical trauma, chemical, radiation, aging, disease or combination thereof.

One embodiment provides for the use of cells prepared by the methods described herein to prepare a medicament to treat a pancreatic disorder or injury, such as pancreatic disorder comprises diabetes (e.g., Type I or Type II diabetes), obesity, pancreatic atresia, pancreas inflammation, alpha1-antitrypsin deficiency, hereditary pancreatitis, pancreatic cancer, pancreatic enzyme deficiency, hyperinsulinism, physical trauma, chemical, radiation, aging, disease or combination thereof. In one embodiment, the medicament further comprises a physiologically acceptable carrier.

DETAILED DESCRIPTION OF THE INVENTION

Figure 1:
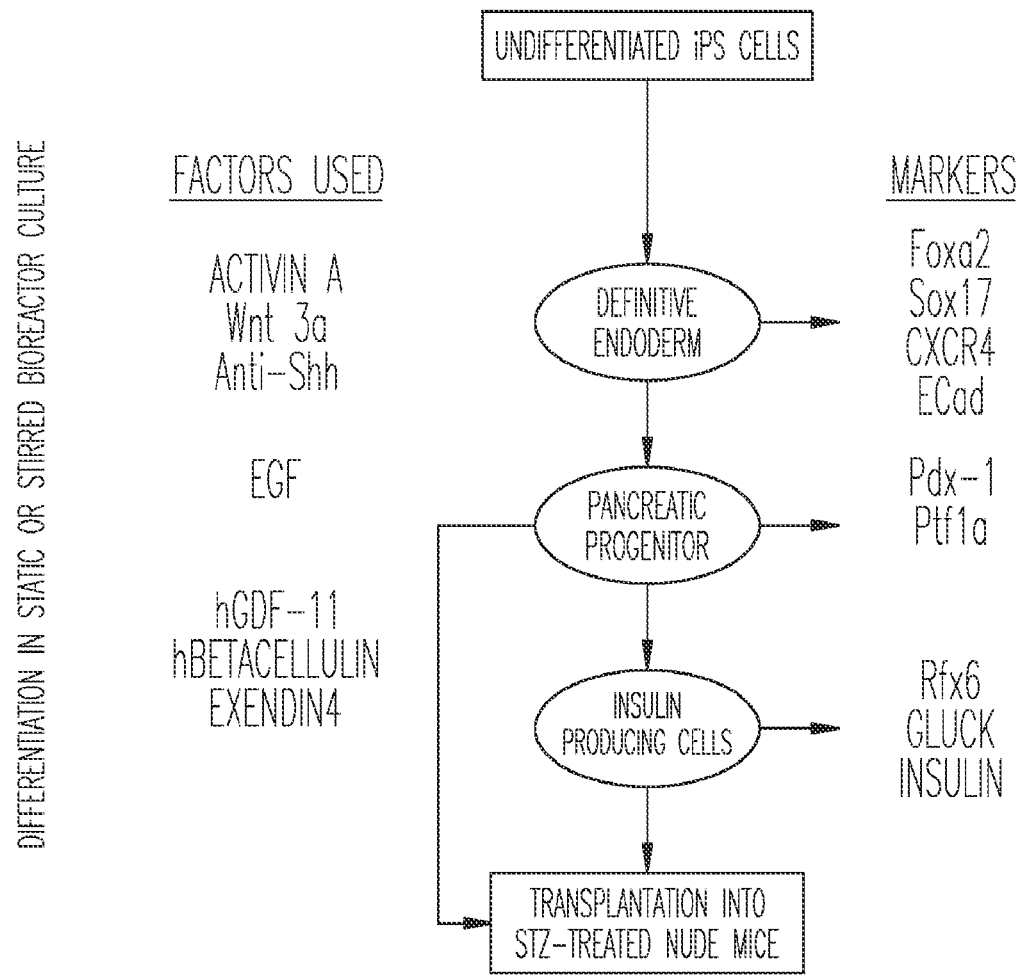
FIG. 1. Schematic representation of the procedure for directed differentiation of human iPS cells in small static culture and stirred bioreactor cultures in vitro, and transplantation in vivo.

Islet transplantation is a promising treatment for diabetes, such as type 1 diabetes, but this application is limited by the availability of donor tissues. Human pluripotent stem cells, including embryonic stem (ES) cells and induced pluripotent stem (iPS) cells have potential to differentiate into virtually all cell types, and several groups have demonstrated that hES and iPS cells differentiate into insulin-producing cells. Herein the derivation of human iPS cells from neonatal foreskin fibroblast cells is described in which the cells were reprogrammed by a combination transduction with human Oct4, Sox3, Nanog and Lin28 genes. One of the iPS cell lines, L-1 was characterized by karyotyping, immunostaining and multilineage differentiation by embryoid body (EB) formation, and expressed human pluripotent stem cell-specific genes such as Oct4, Tra-1-81 and SSEQ-4. Using a four step differentiation process, insulin producing cells were generated. The differentiation to definitive endoderm was identified first based on the expression of specific definitive endoderm markers FoxA2 and Sox17 using qPCR. As many as fifty percent of cells in the first differentiation stage were CXCR4 and E-Cad double positive cells by flow cytometric analysis (FACS), which was higher than human ES differentiation cultures in the same conditions. Pancreatic endoderm was identified by high levels of expression of specific pancreatic progenitor markers Pdx-1 and Ptf1. Finally, after expansion of pancreatic endoderm, insulin producing cells were generated by the addition of maturation factors. Insulin expression was detected by q-PCR and c-peptide release was confirmed by immunostaining. C peptide secreted in supernatant was also detected by ELISA. Thus, insulin producing cells can be generated efficiently from iPS cells in vitro. Further, these cells are capable of reversing diabetes in vivo.

The development of large-scale culture methods for effective cell differentiation and expansion would aid in the achievement of the goal of providing a source of functional cells for cell replacement therapies. Also described herein below is the amplification of human iPS cell differentiation by embryoid body (EB) formation, from small-scale static cultures to dynamic stirred bioreactor cultures. Static and stirred-bioreactor methods were compared by growth rate, cell viability, differentiation efficiency to pancreatic progenitor cells and function analysis in vivo after transplantation into diabetic mice. The results indicated that the bioreactor culture provided 10-100-fold increase in culture volume and cell numbers, with similar in vitro parameters as static cultures, as well as an efficient differentiation scheme. The iPS-derived pancreatic progenitor cells from stirred bioreactors also enhanced survival of diabetic mice by maintaining body weight and by decreasing glucose levels in transplanted mice, resulting in normoglycemia in a subset of mice. The stirred bioreactor chambers can be increased in size to further increase the volume and cell yield. Thus, a directed differentiation protocol for human iPS cells into pancreatic cells can be achieved efficiently in large-scale culture. This system provides a method for producing unlimited allogeneic or patient-specific functional cells for the treatment of diabetes and other diseases.

DEFINITIONS

As used herein, the terms below are defined by the following meanings: "Expansion" refers to the propagation of cells without differentiation, including the proliferation of any cell type without significant further differentiation.

"Progenitor cells" are cells produced during differentiation of a stem cell that have some, but not all, of the characteristics of their terminally-differentiated progeny. Defined progenitor cells, such as "pancreatic progenitor cells," are committed to a lineage, but not to a specific or terminally-differentiated cell type.

An effective amount of an agent (e.g., Activin-A, an agent that inhibits SHH, EGF, Wnt3a, exendin4, GDF11 or betacellulin) is an amount effective to differentiate the cells as recited, when applied alone or in combination with one or more other agents.

"Increased expression" of a marker (e.g., Foxa2, Sox17, CXCR4, ECad, Pdx-1, Ptf1a, Rfx6, Gluck, Insulin) refers to an increase (in mRNA and/or protein) relative to the parent cell (a cell prior to the recited treatment (e.g., contacting with Activin-A etc.) and/or treatments) on an average per cell basis (for example, if the parent cell does not express a marker and the progeny does, there is an increase in expression; or if the progeny expresses more of the marker compared to the parent cell there is also an increase in expression).

"Engraft" or "engraftment" refers to the process of cellular contact and incorporation into an existing tissue or site of interest. In one embodiment, greater than about 5%, greater than about 10%, greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95% or about 100% of administered cells engraft in the pancreas or other tissues.

Persistence refers to the ability of cells to resist rejection and remain or increase in number over time (e.g., days, weeks, months, years) in vivo. Thus, by persisting, the cells can populate the pancreas or other tissues or remain in vivo, such as in barrier devices or other encapsulated forms.

The term "isolated" refers to a cell or cells which are not associated with one or more cells or one or more cellular components that are associated with the cell or cells in vivo. An "enriched population" refers to a relative increase in numbers of the cell of interest relative to one or more other cell types in vivo or in primary culture.

A "subject" or cell source can be a vertebrate, including a mammal, such as a human. Mammals include, but are not limited to, humans, farm animals, sport animals and companion animals. In included in the term "animal" is dog, cat, fish, gerbil, guinea pig, hamster, horse, rabbit, swine, mouse, monkey (e.g., ape, gorilla, chimpanzee, orangutan) rat, sheep, goat, cow and bird.

As used herein, "treat," "treating" or "treatment" includes treating, reversing, ameliorating, or inhibiting an injury or disease-related condition or a symptom of an injury or disease-related condition. Prevention of an injury or disease-related condition or a symptom of an injury or disease-related condition is also carried out by the methods described herein.

An "effective amount" generally means an amount which provides the desired effect. For example, an effective dose is an amount sufficient to affect a beneficial or desired result, including a clinical result. The dose can be administered in one or more administrations and can include any preselected amount of cells. The precise determination of what would be considered an effective dose may be based on factors individual to each subject, including size, age, injury or disease being treated and amount of time since the injury occurred or the disease began. One skilled in the art, particularly a physician, would be able to determine the number of cells that would constitute an effective dose. Doses can vary depending on the mode of administration, e.g., local or systemic; free or encapsulated. The effect can be engraftment or other clinical endpoints, such as reversal or treatment of diabetes. Other effects can include providing beta cells, recruiting endogenous cells, effecting angiogenesis, and/or providing pancreatic progenitors.

"Co-administer" can include sequential, simultaneous and/or separate administration of two or more agents.

The terms "comprises", "comprising", and the like can have the meaning ascribed to them in U.S. Patent Law and can mean "includes", "including" and the like. As used herein, "including" or "includes" or the like means including, without limitation.

Stem Cells/iPS Cells

The embryonic stem (ES) cell has unlimited self-renewal and can differentiate into all tissue types. ES cells are derived from the inner cell mass of the blastocyst or primordial germ cells from a post-implantation embryo (embryonic germ cells or EG cells). ES (and EG) cells can be identified by positive staining with antibodies to SSEA 1 (mouse) and SSEA 4 (human). At the molecular level, ES and EG cells express a number of transcription factors specific for these undifferentiated cells. These include Oct-4 and rex-1. Rex expression depends on Oct-4. Also found are LIF-R (in mouse) and the transcription factors sox-2 and rex-1. Rex-1 and sox-2 are also expressed in non-ES cells. Another hallmark of ES cells is the presence of telomerase, which provides these cells with an unlimited self-renewal potential in vitro.

Adult stem cells, such as "Multipotent adult progenitor cells" (MAPCs) are non-embryonic (non-ES), non-germ and non-embryonic germ (non-EG) cells that can differentiate into one or more ectodermal, endodermal and mesodermal cells types. MAPCs can be positive for telomerase, Oct-3A (Oct-3/4) or a combination thereof. MAPCs have the ability to regenerate all primitive germ layers (endodermal, mesodermal and ectodermal) in vitro and in vivo. In this context they are equivalent to embryonic stem cells and distinct from mesenchymal stem cells. The biological potency of MAPCs has been proven in various animal models, including mouse, rat, and xenogeneic engraftment of human stem cells in rats or NOD/SCID mice (Jiang, Y. et al. 2002). Clonal potency of this cell population has been shown. MAPCs are capable of extensive culture without loss of differentiation potential and show efficient, long term, engraftment and differentiation along multiple developmental lineages without evidence of teratoma formation.

Induced pluripotent stem cell (iPSC) technology is the process of converting an adult specialized cell, such as a skin cell, into a stem cell, a process known as dedifferentiation. Nuclear reprogramming, the process of converting one cell type into another by resetting the pattern of gene expression, can be achieved through forced expression of defined transcription factors. One example is the induced pluripotent stem cells (iPSCs), which can be prepared by transducing up to four genes (e.g., Oct4, Sox2, Klf4 and c-Myc, called OSKM hereafter) into differentiated somatic cells, such as skin fibroblasts. Other genes which can be transduced in place of or in addition to, so as to generate iPS cells, include, for example nanog and lin28

The first mouse iPS cell line was generated in 2006 (Takahashi, 2006), which showed ES-like characteristics in self-renewal, teratoma and chimera formation and differentiation. In 2007 (Takahashi, 2007; Yu, 2007), human iPS cell lines were successfully established, which made the derivation of individual pluripotent stem cells possible from a small skin biopsy. These and many subsequent studies have confirmed human iPS cells are characteristically very similar to ES cells. iPS cells can self-renew and are able to maintain an undifferentiated state when grown under appropriate conditions. As pluripotent cells, they can also differentiate into any cell type, including pancreatic cells, when exposed to environment permissive for, or directing differentiation. Human iPS cell lines have been generated from normal human skin cells and diabetic donors, all of which had the potential to differentiate into insulin-producing cells (Zhang, 2009; Tateishi, 2008; Maehr, 2009).

iPS cells can also have therapeutic uses for the treatment of disease without the need for stem cells derived from an embryonic source. For example, iPSCs can be created from human patients and can be differentiated into many tissues to provide new materials for autologous transplantation, which can avoid immune rejection of the transplanted tissues. For example, pancreatic beta cells differentiated from a patient's iPSCs can be transplanted into the original patient to treat diabetes. However, before these derivatives can be used in clinic, procedures must be developed to generate large numbers of functional cells for preclinical and human trials.

Culture of Cells

Thus, cells or their progeny can be maintained and expanded in culture medium that is available to the art. Such media include, but are not limited to, Dulbecco's Modified Eagle's Medium® (DMEM), DMEM F12 Medium®, Eagle's Minimum Essential Medium®, F-12K Medium®, Iscove's Modified Dulbecco's Medium®, RPMI-1640 Medium®. Many media are also available as a low-glucose formulation, with or without sodium pyruvate.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements, and bovine embryonic fluid. It is understood that sera can be heat-inactivated at about 55-65° C. if deemed necessary to inactivate components of the complement cascade.

Additional supplements can also be used advantageously to supply the cells with the trace elements for optimal growth and expansion. Such supplements include insulin, transferrin, sodium selenium and combinations thereof. These components can be included in a salt solution such as, but not limited to Hanks' Balanced Salt Solution® (HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids; however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine and L-valine. It is well within the skill of one in the art to determine the proper concentrations of these supplements.

Antibiotics are also typically used in cell culture to mitigate bacterial, mycoplasmal and fungal contamination. Typically, antibiotics or anti-mycotic compounds used are mixtures of penicillin/streptomycin, but can also include, but are not limited to, amphotericin (Fungizone®), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin and zeocin. Antibiotic and antimycotic additives can be of some concern, depending on the type of work being performed. One possible situation that can arise is an antibiotic-containing media wherein bacteria are still present in the culture, but the action of the antibiotic performs a bacteriostatic rather than bacteriocidal mechanism. Also, antibiotics can interfere with the metabolism of some cell types.

Hormones can also be advantageously used in cell culture and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine and L-thyronine.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others.

Also contemplated is the use of feeder cell layers. Feeder cells are used to support the growth of fastidious cultured cells, including stem cells. Feeder cells are normal cells that have been inactivated by, for example, γ-irradiation or x-irradiation. In culture, the feeder layer serves as a basal layer for other cells and supplies cellular factors without further growth or division of their own. Examples of feeder layer cells are typically human diploid lung cells, mouse embryonic fibroblasts, Swiss mouse embryonic fibroblasts, but can be any post-mitotic cell that is capable of supplying cellular components and factors that are advantageous in allowing optimal growth, viability and expansion of stem cells.

Cells in culture can be maintained either in suspension or attached to a solid support, such as extracellular matrix components and synthetic or biopolymers. Stem cells sometimes need additional factors that encourage their attachment to a solid support, such as type I, type II and type IV collagen, concanavalin A, chondroitin sulfate, fibronectin, "superfibronectin" and fibronectin-like polymers, gelatin, laminin, poly-D and poly-L-lysine, thrombospondin and vitronectin.

The maintenance conditions of stem cells can also contain cellular factors that allow stem cells to remain in an undifferentiated form. It is advantageous under conditions where the cell must remain in an undifferentiated state of self-renewal for the medium to contain for example epidermal growth factor (EGF), platelet derived growth factor (PDGF), FGF (such as bFGF (FGF-2), leukemia inhibitory factor (LIF; in selected species), and combinations thereof. It is apparent to those skilled in the art that supplements that allow the cell to self-renew but not differentiate should be removed from the culture medium prior to differentiation.

Stem cell lines and other cells can benefit from co-culturing with another cell type. Such co-culturing methods arise from the observation that certain cells can supply cellular factors that allow the stem cell to differentiate into a specific lineage or cell type. These cellular factors can also induce (suppress) expression of cell-surface, cytoplasmic and nuclear molecules, which can used as markers and are therefore readily identified by through various methods, including, such as by monoclonal antibodies. They may also regulate cellular functions. Generally, cells for co-culturing are selected based on the type of lineage one skilled in the art wishes to induce, and it is within the capabilities of the skilled artisan to select the appropriate cells for co-culture.

Differentiation of Stem Cells to Pancreatic Cells

Stem/iPs cells and pancreatic progenitor cells differentiated from stem/iPS cells are useful as a source of pancreatic cells. The maturation, proliferation and differentiation of stem/iPS cells may be effected through culturing stem/iPS cells with appropriate factors (examples of nucleotide/protein accession numbers provided) including, but not limited to, activin-A (generally two subunits of NM_002192) or other members TGFβ family of cytokines (e.g., BMP-4), including, but not limited the nodal subset of the TGFβ family of cytokines (activin and nodal related factors, including, but not limited to, nodal, activina and activinb), Wnt3a (or other members of the Wnt family, including, but not limited to, WNT1 (NM_005430; NM_021279; NP_005421; NP_067254), WNT2 (NM_003391; NM_023653; NP_003382; NP_076142), WNT2B (NM_004185; NM_009520; NP_004176; NP_033546), WNT3 (NM_030753; NM_009521; NP_110380; NP_033547), WNT3A (NM_033131; NM_009522; NP_149122; NP_033548), WNT4 (NM_030761; NM_009523; NP_110388; NP_033549), WNT5A (NM_003392; NM_009524; NP_003383; NP_033550), WNT5B (NM_030775; NM_009525; NP_110402; NP_033551), WNT6 (NM_006522), WNT7A (NM_004625; NM_009527; NP_004616; NP_033553), WNT7B (NM_058238; NM_009528; NP_478679; NP_033554), WNT8A, WNT8B (NM_003393; NM_011720; NP_003384; NP_035850), WNT9A (NM_003395; NM_139298; NP_003386; NP_647459), WNT9B, WNT10A (NM_025216; NM_009518; NP_079492 NP_033544), WNT10B (NM_003394; NM_011718; NP_003385; NP_035848), WNT11 (NP_004617; NP_033545 NP_004617; NP_033545), WNT16 (NM_016087; NM_053116; NP_057171 NP_444346)), an agent that inhibits sonic hedgehog activity (including, but not limited to, cyclopamine and anti-SHH antibody), HGF (Hepatocyte growth factor/scatter factor; NM_000601; NM_010427; NP_000592; NP_034557), a member of the Epidermal growth factor (EGF) family (including, but not limited to, EGF (NM_001963; NM_010113; NP_001954; NP_034243), Heparin-binding EGF-like growth factor (HB-EGF; NM_001945; NM_010415; NP_001936; NP_034545), transforming growth factor-α (TGF-α; NM_003236; NM_031199; NP_003227; NP_112476), Amphiregulin (AR; NM_001657; NM_009704; NP_001648; NP_033834), Epigen (NM_001013442), Betacellulin (BTC; NM_001729; NM_007568; NP_001720; NP_031594), neuregulin-1 (NRG1; NM_004495; XM_620642; NP_004486; XP_620642), neuregulin-2 (NRG2; XM_001129975; XP_001129975), neuregulin-3 (NRG3; NM_001165972; NM_008734; NP_001010848; NP_032760), neuregulin-4 (NRG4; NM_138573; NM_032002; NP_612640; NP_114391), any protein which contains one or more repeats of the conserved amino sequence $CX_7CX_{4-5}CX_{10-13}CXCX_8GXRC$, where X represents any amino acid, or a combination thereof), or other mitogenic proteins, exendin (including, but not limited to, exendin 4 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2; SEQ ID NO:11) and exenatide (a synthetic 39-amino acid peptide which closely resembles exendin-4 and is marketed by Amylin Pharmaceuticals and Eli Lilly and Company as Byetta™ for the treatment of diabetes; CAS number 141732-76-5)), Growth differentiation factor 11 (GDF11) also known as bone morphogenetic protein 11 (BMP-11) or other members of the bone morphogenetic protein/transforming growth factor beta (BMP/TGFbeta) superfamily, and/or betacellulin (or other members of the EGF family). These proteins can generally be used in the amount of, for example, about 0.5 to about 200 ng/ml or about 5 nM to about 30 nM.

The transforming growth factor beta (TGF-β) family is a large family of structurally related cell regulatory proteins ((LIVM)-x(2)-P-x(2)-[FY]-x(4)-C-x-G-x-C). Proteins from the TGF-beta family are generally active as a homo- or heterodimer; the two chains being linked by a disulfide bond. Members of the TGFβ family of cytokines (with examples of nucleotide/protein accession numbers for these members) include, but are not limited to, AMH (NM_000479); ARTN; BMP10 (NM_014482; NM_009756; NP_055297; NP_033886); BMP15 (NM_005448; NM_009757; NP_005439; NP_005439); BMP2 (NM_001200; NM_007553; NP_001191; NP_031579); BMP3 (NM_001201; NM_173404; NP_001192; NP_775580); BMP4 (NM_001202; NM_007554; NP_001193; NP_031580); BMP5 (NM_021073; NM_007555; NP_066551; NP_031581); BMP6 (NM_001718; NM_007556; NP_001709; NP_031582); BMP7 (NM_001719; NM_007557; NP_001710; NP_031583); BMP8A (NM_181809; NM_007558; NP_861525; NP_031584); BMP8B (NM_001720; NM_001720); GDF1 (NM_001492; NM_008107; NP_001483; NP_032133); GDF10 (NM_004962; NM_145741; NP_004953; NP_665684); GDF11 (NM_005811; NM_010272; NP_005802; NM_010272); GDF15 (NM_004864; NM_011819; NP_004855; NP_035949); GDF2 (NM_016204; NM_019506; NP_057288; NP_062379); GDF3 (NM_020634; NM_008108; NP_065685; NP_032134); GDF3A; GDF5 (NM_000557; NM_008109; NP_000548; NP_032135); GDF6 (NM_001001557; NM_013526; NP_038554); GDF7 (NM_182828; NM_013527; NP_878248; NP_038555); GDF8 (NM_005259; NM_010834; NP_005250; NP_034964); GDF9 (NM_005260; NM_008110; NP_005251; NP_032136); GDNF (NM_000514; NM_010275; NP_000505; NP_034405); INHA (NM_002191; NM_010564; NP_002182; NP_034694); INHBA (NM_002192; NM_008380; NP_002183; NP_032406); INHBB (NM_002193; XM_984243; NP_002184; XP_989337); INHBC (NM_005538; NM_010565; NP_005529; NP_034695); INHBE; LEFTY1; LEFTY2; MSTN (NM_005259; NM_010834; NP_005250; NP_034964); NODAL (NM_018055; NM_013611; NP_060525; NP_038639); NRTN (NM_004558); PSPN; TGFB1 (NM_000660; NM_011577; NP_000651; NP_035707); TGFB2 (NM_003238; NM_009367; NP_003229; NP_033393); and TGFB3 (NM_003239; XM_994378; NP_003230; XP_999472).

For example, sequences for use in the invention have at least about 50% or about 60% or about 70%, about 71%, about 72%, about 73%, about 74%, about 75%, about 76%, about 77%, about 78%, or about 79%, or at least about 80%, about 81%, about 82%, about 83%, about 84%, about 85%, about 86%, about 87%, about 88%, or about 89%, or at least about 90%, about 91%, about 92%, about 93%, or about 94%, or at least about 95%, about 96%, about 97%, about 98%, or about 99% sequence identity compared to the accession numbers provided herein and/or any other such sequence available to an art worker, using one of alignment programs available in the art using standard parameters. In one embodiment, the differences in sequence are due to conservative amino acid changes. In another embodiment, the protein sequence or DNA sequence has at least 80%, at least 85%, at least 90%, at least 95% sequence identity with the sequences disclosed herein and is bioactive (e.g., retains activity).

Methods of alignment of sequences for comparison are available in the art. Thus, the determination of percent identity between any two sequences can be accomplished using a mathematical algorithm. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

An agent that inhibits sonic hedgehog (SHH) activity (e.g., signaling) includes any agent (e.g., a peptide, protein, including antibodies, small molecule, drug, chemical, or nucleic acid, such as DNA or RNA) which inhibits the function or expression of sonic hedgehog (including, but not limited to, providing signal(s) in the patterning of the early embryo, such as patterning of the ventral neural tube, the anterior-posterior limb axis, and the ventral somites). Such agents include, but are not limited to, an anti-sonic hedgehog antibody, cyclopamine (CPA), analogs thereof, such as cyclopamine-4-ene-3-one or other steroidal alkaloids. As used herein, "inhibit" refers to a reduction (e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100%) in the activity of sonic hedgehog as compared to the activity of SHH in the absence of an agent that inhibits SHH activity.

As described in Example 1 and 2 herein below, stem cells were differentiated into pancreatic progenitor cells and beta-cells in vitro. Briefly, stem cells were cultured in medium containing Activin-A (about 0.5 ng/ml to about 200 ng/ml, such as about 50 ng/ml to about 100 ng/ml, including about 100 ng/ml) and Wnt3a (about 10 ng/ml to about 100 ng/ml, such as about 20 ng/ml to about 50 ng/ml or about 50 ng/mL) for about 3 days, followed by about six days of culture in Activin A, Wnt 3a and anti-SHH antibody (about 2.5 mg/ml to about 10 ng/ml). The cells obtained therefrom were next cultured in medium containing EGF (e.g., about 5 to about 100 ng/mL, including about 50 ng/mL) for about 6 days. The cells obtained therefrom were then cultured in medium containing GDF-11 (e.g., about 5 to about 100 ng/mL, including about 50 ng/mL), exendin4 (e.g., about 5 nM to about 50 nM, including about 10 nM), and betacellulin (e.g., about 10 ng/mL to about 100 ng/mL, including about 50 ng/mL) for about six days.

Methods of identifying and subsequently separating differentiated cells from their undifferentiated counterparts can be carried out by methods well known in the art and described herein. Cells that have been induced to differentiate can be identified by selectively culturing cells under conditions whereby differentiated cells outnumber undifferentiated cells. Similarly, differentiated cells can be identified by morphological changes and characteristics that are not present on their undifferentiated counterparts, such as cell size, the number of cellular processes, the complexity of intracellular organelle distribution, and the production of insulin or C-peptide and the secretion of insulin or C-peptide in response to glucose.

Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS) and enzyme-linked immunosorbent assay (ELISA). From the standpoint of transcriptional upregulation (or increase protein expression) of specific genes, differentiated cells often display levels of gene expression that are different (increased or decreased expression of mRNA or protein) from undifferentiated cells, such as insulin-1, insulin-2, glucagon, somatostatin, NeuroD1, Pdx-1, Ngn3, NRx6.1, NRx2.2, rfx-6, ptf1, glucokinase (glck), chromogranin, Maf, and/or glucose transporter. Reverse-transcription polymerase chain reaction (RT-PCR) can be used to monitor such changes in gene expression during differentiation. In addition, whole genome analysis using microarray technology can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads, and combinations thereof.

Use of Stem/iPS Cell Derived Pancreatic Cells

The pancreatic progenitor or insulin producing cells of the invention can be used to repopulate a pancreas by either direct introduction into the area of damage or by systemic administration, which allows the cells to home to the area of damage. Accordingly, the invention provides methods of treating a subject in need of pancreatic cells comprising administering to a subject an effective amount of the pancreatic progenitor cells of the invention.

For the purposes described herein, either autologous, allogeneic or xenogeneic cells can be administered to a patient, either in undifferentiated, terminally differentiated or in a partially differentiated form, genetically altered or unaltered, by direct introduction to a site of interest, e.g., on or around the surface of an acceptable matrix, or systemically, in combination with a pharmaceutically acceptable carrier so as to repair, replace or promote the growth of existing and/or new pancreatic cells.

Generally, the invention provides methods to treat a pancreatic disorder. The term "pancreatic disorder" or "pancreatic disease" refers to a state where pancreatic function is impaired. Examples of "pancreatic disorders" or "pancreatic diseases" that can be treated with the compositions and methods of the invention include, but are not limited to, diabetes (including Type 1, Type 2, MODY and other genetic causes of diabetes), obesity, pancreatic atresia, pancreas inflammation, alpha1-antitrypsin deficiency, acute, chronic or hereditary pancreatitis, pancreatic cancer (including endocrine tumors of the pancreas), pancreas malfunction due to cystic fibrosis or Shwachman Diamond syndrome, pancreatic insufficiency or pancreatic enzyme deficiency, pancreatic cysts, hyperinsulinism, pancreatic digestive diseases, genetic disorders of the exocrine pancreas and pancreatic injury, including, but not limited to, injury as a result of physical trauma (including, but not limited to, surgery), chemical, radiological, aging, and/or disease.

Administration of the Cells

Stem cell derived pancreatic progenitors can be administered to a subject by a variety of methods available to the art, including but not limited to localized injection, catheter administration, systemic injection, intraperitoneal injection, parenteral administration, intra-arterial injection, intravenous injection, transvascular injection, intramuscular injection, subcutaneous placement/injection, surgical injection into a tissue of interest (e.g., injection into the pancreas) or via direct application to tissue surfaces (e.g., during surgery or on a wound).

Stem cell derived pancreatic progenitors can be administered either peripherally or locally through the circulatory system. "Homing" of stem cells would concentrate the implanted cells in an environment favorable to their growth and function. Pre-treatment of a patient with cytokine(s) to promote homing is another alternative contemplated in the methods of the present invention. Certain cytokines (e.g., cellular factors that induce or enhance cellular movement, such as homing of other stem cells, progenitor cells or differentiated cells) can enhance the migration of iPS cell derived pancreatic progenitors or their progeny. Cytokines include, but are not limited to, stromal cell derived factor-1 (SDF-1), stem cell factor (SCF), angiopoietin-1, placenta-derived growth factor (PlGF) and granulocyte-colony stimulating factor (G-CSF). Cytokines also include any which promote the expression of endothelial adhesion molecules, such as ICAMs, VCAMs and others, which facilitate the homing process.

Viability of newly forming tissues can be enhanced by angiogenesis. Factors promoting angiogenesis include, but are not limited to, VEGF, aFGF, angiogenin, angiotensin-1 and -2, betacellulin, bFGF, Factor X and Xa, HB-EGF, PDGF, angiomodulin, angiotropin, angiopoetin-1, prostaglandin E1 and E2, steroids, heparin, 1-butyryl-glycerol and nicotinic amide.

Factors that decrease apoptosis can also promote the formation of new tissue, such as pancreatic tissues. Factors that decrease apoptosis include but are not limited to β-blockers, angiotensin-converting enzyme inhibitors (ACE inhibitors), AKT, HIF, carvedilol, angiotensin II type 1 receptor antagonists, caspase inhibitors, cariporide and eniporide.

Exogenous factors (e.g., cytokines, differentiation factors (e.g., cellular factors, such as growth factors or angiogenic factors that induce lineage commitment), angiogenesis factors and anti-apoptosis factors) can be administered prior to, after or concomitantly with the cells.

A method to potentially increase cell survival is to incorporate cells into a biopolymer or synthetic polymer. Depending on the patient's condition, the site of injection might prove inhospitable for cell seeding and growth because of scarring or other impediments. Examples of biopolymer include, but are not limited to, fibronectin, fibrin, fibrinogen, thrombin, collagen and proteoglycans. This can be constructed with or without included cytokines, differentiation factors, angiogenesis factors or anti-apoptosis factors. Additionally, these can be in suspension. Another alternative is a three-dimensional gel with cells entrapped within the interstices of the cell biopolymer admixture. Again cytokines, differentiation factors, angiogenesis factors, anti-apoptosis factors or a combination thereof can be included within the gel. These can be deployed by injection via various routes described herein.

The cells can also be encapsulated with a capsule that is permeable to nutrients and oxygen while allowing appropriate cellular products (for example, insulin in the case of islet cells) to be released into the bloodstream or to adjacent tissues. In one embodiment, the capsular material is restrictive enough to exclude immune cells and antibodies that could reject and destroy the implant. Such encapsulation can be achieved using, for example, polymers (Chang, 2000). Such polymeric encapsulation systems include, but are not limited to, alginate (e.g., alginate bead), polysaccharide hydrogels, chitosan, calcium or barium alginate, a layered matrix of alginate and polylysine, a photopolymerizable poly(ethylene glycol) (PEG) polymer (Novocell, Inc.), a polyanionic material termed Biodritin (U.S. Pat. No. 6,281,341), polyacrylates, a photopolymerizable poly(ethylene glycol) polymer, and polymers such as hydroxyethyl methacrylate methyl methacrylate. Another approach to encapsulate cells involves the use of photolithography techniques adapted from the semiconductor industry to encapsulate living cells in silicon capsules that have pores only a few nanometers wide (Desai 2002). Also, suitable immune-compatible polycations, including but not limited to, poly-1-lysine (PLL) polycation or poly-1-ornithine or poly(methylene-co-guanidine) hydrochloride, may be used to encapsulate cells.

Additionally, cells can be encapsulated with biocompatible semipermeable membranes to surround encapsulated cells, sometimes within a capillary device, to create a miniature artificial organ, such as one that would include functional pancreas or liver cells (e.g., a liver or pancreatic artificial device). This is often called macroencapsulation. The membrane lets glucose, oxygen, and insulin pass in and out of the blood stream, and preferably keeps out the antibodies and T cells of the immune system, which may destroy the cells (e.g., islets). Such membranes can be used in a perfusion device, a capsule that is grafted to an artery where it makes direct contact with the body's circulating blood; in this way, the device can draw nutrients from the blood and release insulin to circulate throughout the body. Another method provides for coating a small group of islet cells (macroencapsulation) or individual islet cells (microencapsulation) and implanting them inside the abdominal cavity. In these devices nutrients and insulin would be exchanged by way of the body fluids permeating the tissues in which they are implanted.

The cells can also be administered in via a device or scaffolding substance (that may or may not be a polymer) to contain the cells (e.g., the cells can be placed in the device prior to implantation). In one embodiment, this device/substance is retrievable. In another embodiment, it is absorbable. In another embodiment, a site may be created surgically to contain the cells. In one embodiment, the cells (pancreatic progenitor cells/insulin producing cells are transplanted with additional cell types, including, but not limited to, mesenchymal stem cells or endothelial cells.

The quantity of cells to be administered will vary for the subject being treated. In a preferred embodiment, between about $10^4$ to about $10^8$, more preferably about $10^5$ to about $10^7$ and most preferably, about $3 \times 10^7$ stem cells and optionally, about 50 to about 500 μg/kg per day of a cytokine can be administered to a human subject. However, the precise determination of what would be considered an effective dose may be based on factors individual to each patient, including their size, age, disease or injury, amount of damage, amount of time since the damage occurred and factors associated with the mode of delivery (direct injection—lower doses, intravenous—higher doses). Dosages can be readily ascertained by those skilled in the art from this disclosure and the knowledge in the art.

When administering a therapeutic composition of the present invention, it can generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used should be compatible with the cells.

Sterile injectable solutions can be prepared by incorporating the cells utilized in practicing the present invention in the required amount of the appropriate solvent with various amounts of the other ingredients, as desired.

In one embodiment, the cells described herein can be administered initially, and thereafter maintained by further administration of cells. For instance, the cells can be administered by one method of injection, and thereafter further administered by a different or the same type of method.

Compositions are conveniently provided as liquid preparations, e.g., isotonic aqueous solutions, suspensions, emulsions or viscous compositions, which may be buffered to a selected pH. Liquid preparations are normally easier to prepare than gels, other viscous compositions and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected and the desired viscosity. Viscous compositions are normally prepared from solutions by the addition of such thickening agents.

A pharmaceutically acceptable preservative or cell stabilizer can be employed to increase the life of the compositions. Preferably, if preservatives are necessary, it is well within the purview of the skilled artisan to select compositions that will not affect the viability or efficacy of the cells as described in the present invention.

Those skilled in the art will recognize that the components of the compositions should be selected to be chemically inert. This will present no problem to those skilled in chemical and pharmaceutical principles, or problems can be readily avoided by reference to standard texts or simple experiments (not involving undue experimentation), from this disclosure and the documents cited herein.

Monitoring of Subject after Administration of Cells

Following transplantation, the growth or differentiation of the administered cells or or the therapeutic effect of the cells may be monitored. For example, blood glucose, serum glucose, HbA1c (a measure of glycosylated protein) and/or serum insulin may be monitored.

Following administration, the immunological tolerance of the subject to the cells may be tested by various methods known in the art to assess the subject's immunological tolerance to the cells. In cases where the subject's tolerance of the cells is suboptimal (e.g., the subject's immune system is rejecting the exogenous cells), therapeutic adjunct immunosuppressive treatment, which is known in the art, of the subject may be performed.

EXAMPLES

The following examples are provided in order to demonstrate and further illustrate certain embodiments and aspects of the present invention and are not to be construed as limiting the scope thereof.

Example I

Differentiation of Stem Cells to Pancreatic Cells

Materials and Methods

Lentivirus production: Each recombinant lentivirus expressing human Oct4, Sox2, Nanog, and Lin28 was generated by transfecting the constructors (Addgene, 16579, 16577, 16578, 16580) together with packaging plasmid pΔNRF and MD.G into 293FT cells. Briefly, $4.5 \times 10^6$ 293FT cells were seeded using DMEM medium supplemented with 10% FBS in 15 cm plates. The transfection was conducted the next day using a calcium-phosphate-mediated method. Twenty hours after transfection, the medium was changed to DMEM with 2% FBS. Viral supernatants were harvested at 24 and 48 hours post transfection and concentrated by ultracentrifugation at 22,000 rpm for 2 hours.

Derivation of iPS cell lines: $1.25 \times 10^5$ neonatal human dermal fibroblast (NHDF, Lonza) cells were seeded on a gelatin coated 6-well plate the day before lentiviral transduction in growth medium containing high-glucose DMEM, 10% FBS, 1×NEAA. A mixture of 4 different recombinant lentiviruses expressing human Oct4, Sox2, Nanog, and Lin28 was used to infect the NHDF cells in the presence of 8 µg/ml polybrene (Sigma). After overnight incubation with the mixture, the medium containing viruses was replaced with fresh growth medium. Four days after transduction, $5.5 \times 10^4$ cells were collected by trypsin (Invitrogen) digestion and transferred onto irradiated mouse embryonic fibroblast (MEF) cells in each well of 6-well plates with human embryonic stem (hES) cell medium (DMEM/F12 medium containing 20% knockout serum replacement, 0.1 mM nonessential amino acids, L-glutamine, 0.1 mM β-mercaptoethanol and 4 ng/ml basic fibroblast growth factor). Colonies with typical hES cell morphology appeared 15 days post-transduction and were picked for expansion on day 26.

Cell culture and differentiation: iPS cell lines were cultured in iPS medium (DMEM/F12 medium containing 20% knockout serum replacement, 0.1 mM nonessential amino acids, L-glutamine, 0.1 mM β-mercaptoethanol and 100 ng/ml basic fibroblast growth factor). Cultures were maintained on irradiated primary (MEF) feeders and passaged enzymatically using 10 µg/ml collagenase IV (Invitrogen).

Differentiation was achieved using embryoid body (EB) formation. Spontaneous differentiation was initiated by dissociating human iPS cells using collagenase, and putting them into 24-well Ultra-low attachment plate in differentiation medium (DMEM supplemented with 20% FBS, 1 mM L-glutamine, 0.1 mM nonessential amino acids, 0.1 mM β-mercaptoethanol). Directed differentiation was conducted in 2% FBS differentiation medium with the following steps: Stage 1: from day 0 to day 3, the culture was supplemented with 100 ng/ml Activin A and 50 ng/ml Wnt3a. Stage 2: From day 3 to day 9, the medium was supplemented 2.5 mg/ml anti-human Shh in addition to Activin A and Wnt3a. Stage 3: from day 9 to day 15, the medium was supplemented with 50 ng/ml hEGF and 50 ng/ml heparin sulfate. Stage 4: from day 15 to day 21, the medium contained 50 ng/ml hGDF-11, 50 ng/ml hBetacellulin and 10 nM Exendin. All cytokines except Exendin (Sigma) were from R&D Systems. The stimulation schedule is as shown in Table 1. The medium was refreshed every 3 days. Samples of EBs were harvested every 3 days for analysis at each stage to identify specific cell populations.

RNA Extraction and gene expression analysis: Total RNA was extracted from cell samples using the RNeasy Micro kit (Qiagen) according to the protocol provided in the kit and 0.5-5 µg of the extracted total RNA was used in reverse transcription to synthesize cDNA using the SuperScript III First-stand Synthesis System for RT-PCR kit (Invitrogen). Quantitative PCR (qPCR) was carried out with cDNA using SYBR Green (Applied Biosystems) on an Eppendorf Mastercycler (realplex$^2$).

Immunofluorescence: For iPS cell line characterization, colonies growing on feeders were fixed using 4% paraformaldehyde and then washed with PBS. Immunostaining was performed using primary antibodies against Oct4 (Chemicon), Nanog (R&D systems), Sox2 (R&D systems), Tra-1-81 (Chemicon) for overnight at 4° C. first, followed by anti-mouse or anti-goat Alexa Fluor 488 for 1 hour in the dark after washing with PBS plus 0.05% Tween-20. For SSEA-4 staining, after fix, PE conjugated antibody was performed directly for 1 hour in the dark after washing with PBS plus 0.05% Tween-20.

For differentiation analysis, harvested EBs were washed three times in Dulbecco's phosphate buffered saline (PBS), fixed for 30 minutes in 4% paraformaldehyde, and processed for paraffin embedding. Sections (7 µm) were retrieved with Antigen Retrieval Reagent (R&D systems) at 95° C. for 5 minutes, blocked with PBS plus 1% BSA, 10% donkey serum and Triton X-100 for 30 minutes, and incubated with primary antibody against proinsulin (rat anti-human proinsulin, GN-ID4, DSHB) and Pdx-1 (Biotinylated goat anti-human Pdx-1) (R&D) for 2 hour at room temperature, followed by streptavidin Alexa Fluor 488 for Pdx-1 and secondary antibodies anti-rat IgG-PE (BD Bioscience) for proinsulin. Staining was observed by fluorescence microscopy.

Detection of C-peptide concentration in culture supernatants by ELISA: Culture supernatants were harvested at different time points and stored at −80° C. until use. C-peptide concentration was detected according to the instructions from the human C-peptide kit (Millipore).

Transplantation of differentiated L-1 cells into mice: Mice were socially housed and participated in a complete enrichment program. Dietary enrichment included provision of black oil sunflower seeds (Bio-Serv, Frenchtown, N.J.) and Enrich Mix (1922 Harlan Teklad, Madison, Wis.) daily. Environmental enrichment included a crawl ball, polycarbonate igloo, or paper hut.

Diabetes Induction in Nude Mice: Adult male nude mice, 29.7-33.5 grams, were obtained from the Charles River Laboratories (Wilmington, Mass., USA). Diabetes induction was accomplished using a single IP infusion of streptozotocin (STZ, Zanosar; Sicor Pharmaceuticals, Irvine, Calif., USA) 240 mg/kg bolus. Following the administration of STZ, animals were closely monitored for adverse events Animals received supportive hydration (1-3 ml normal saline IP) concomitantly and as clinically indicated post STZ injection. Blood glucose and weight were measured daily or as clinically indicated from STZ to the scheduled experimental endpoint. Blood glucose levels were measured by bleeding the tail vein. Mice with a blood glucose level >300 mg/dL for 2 consecutive days were considered diabetic, at which time insulin injections were initiated. In diabetic mice, 0.5U glargine (Lantus, Aventis, Parsippany, N.J.) was injected subcutaneously, daily or as clinically indicated, until beta cell transplant, or in some experiments until glucose levels were stabilized below 350 mg/dL. Blood collection, via tail or facial vein bleed, was performed approximately every 14 days for RIA analysis for human C-peptide using the Millipore human RIA kit according to the manufacturers instructions.

Transplant Under Renal Capsule of Nude Mice: Isoflurane was delivered via precision anesthetic vaporizer for anesthesia. After full aseptic preparation using Technicare surgical scrub (C are Tech Laboratories, St Louis, Mo.), the mouse was placed laterally on surgical field. Using a sterile dissecting forceps and scissors a 1 cm incision in the skin and peritoneum was created to expose the kidney. The kidney was gently externalized using palpation. A small nick (1-3 mm) to the kidney capsule was made and the collected differentiated iPS cells, approximately $1-2 \times 10^6$ cells (FIG. 3) or $3-8 \times 10^6$ (FIG. 4) cells were placed under the kidney capsule, using PE160 tubing attached to a Hamilton syringe. The kidney was reintroduced into the peritoneum, the muscle layer was approximated, and the skin layer was closed with absorbable suture. Analgesia was accomplished using ketoprofen 5 mg/kg SC a single dose pre-operatively, and as needed post operatively.

Transplant in Epididymal Fat Pad of Nude Mice: Isoflurane was delivered via precision anesthetic vaporizer for anesthesia. After full aseptic preparation using Technicare surgical scrub (C are Tech Laboratories, St Louis, Mo.), the mouse was placed dorsally on surgical field. Using a sterile dissecting forceps and scissors a 1 cm incision in the skin and fascia was created on the ventral midline in the groin area. The epididymal fad pad (EFP) was gently exposed and kept moist with physiologic saline. A purse string suture was used at the periphery of the EFP to create a pouch. Between 4 and $8 \times 10^6$ differentiated iPS cells were loaded into PE160 tubing, the PE tubing placed into the pouch, and cells were delivered to the EFP pouch. The purse string was ligated, closing the opening and marking site of implantation. The fascia and skin were closed with absorbable suture. Analgesia was accomplished using ketoprofen 5 mg/kg SC a single dose pre-operatively, and as needed post operatively.

Nephrectomy: Isoflurane was delivered via precision anesthetic vaporizer for anesthesia. After full aseptic preparation using Technicare surgical scrub (C are Tech Laboratories, St Louis, Mo.), the mouse was placed laterally on surgical field. Using a sterile dissecting forceps and scissors a 1 cm incision was made through skin and muscle at the previous incision site. The kidney was gently exposed and the renal vessels were ligated. The kidney was then removed, the muscle layer was approximated and the skin layer was closed with absorbable suture. Analgesia was accomplished using ketoprofen 5 mg/kg SC a single dose pre-operatively, and as needed post operatively. The graft and kidney were collected for immunohistochemistry and PCR analysis.

An efficient method for differentiating human embryonic stem (hES) cells into pancreatic endoderm cells based on sequential exposure to cytokines that regulate mammalian pancreatic fate in vivo was developed using fewer cytokines than other published protocols (Table 1).

TABLE 1

Strategy for differentiation of pluripotent cells into insulin-producing cells.

|  |  | Cytokine | Fate Induced |
|---|---|---|---|
| Stage 1 | Day 0-3 | 100 ng/ml Activin A<br>50 ng/ml Wnt 3a | Endoderm |
| Stage 2 | Day 3-9 | 100 ng/ml Activin A<br>50 ng/ml Wnt 3a<br>2.5 ug/ml anti-Shh | Definitive endoderm<br>Pancreatic endoderm |
| Stage 3 | Day 9-15 | 50 ng/ml EGF | Expansion of Pancreatic endoderm |
| Stage 4 | Day 15-21 | 50 ng/ml GDF-11<br>50 ng/ml Betacellulin<br>10 nM Exendin4 | Pancreatic cells Maturation of β cells |

Figure 6:
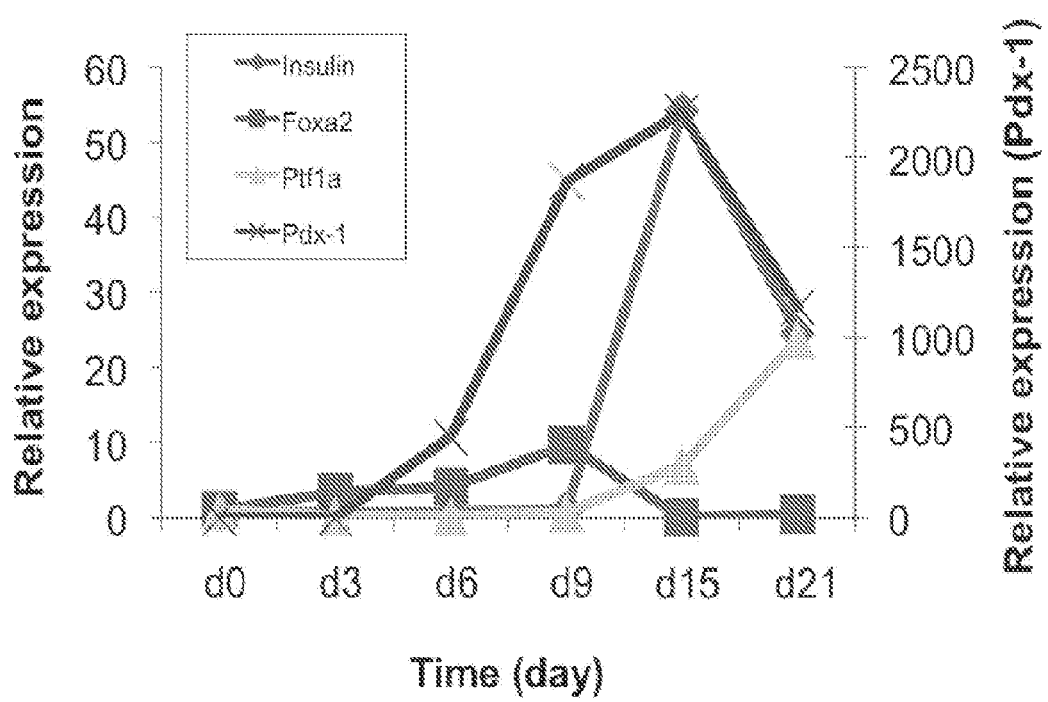
FIG. 6. Directed differentiation of human H9 ES cells in vitro progresses through developmental stages. Quantitative PCR analysis of the definitive endoderm (Foxa2), pancreatic endoderm (Pdx-1, Ptf1a) and endocrine (Insulin) markers during differentiation of human H9 embryonic stem cells demonstrated sequential stages of pancreatic development. Relative levels of gene expression were normalized to the GAPDH mRNA levels. The value of undifferentiated (day 0) H9 cells is set at 1.

This four step method was used to differentiate the hES cell line H9 into insulin producing pancreatic cells. Specific differentiated intermediates were identified by sequential expression of a series of transcriptional factors. Foxa2 was used as a marker for definitive endoderm. Following maturation to pancreatic endoderm, expression of the transcription factors Pdx-1 and Ptf1a were observed, while mature beta cells were indicated by the expression of Pdx-1and insulin. Differentiating H9 cells exhibited a similar sequential gene expression pattern to the HSF-6 hES line under the same conditions (not shown) and during in vivo mouse development (Habener et al. (2005) and Jensen (2004) (see FIG. 6)). These data suggest that pancreatic development is occurring in embryoid bodies (EBs), and that the differentiation scheme is robust enough to direct differentiation in multiple pluripotent lines.

Figure 7B:
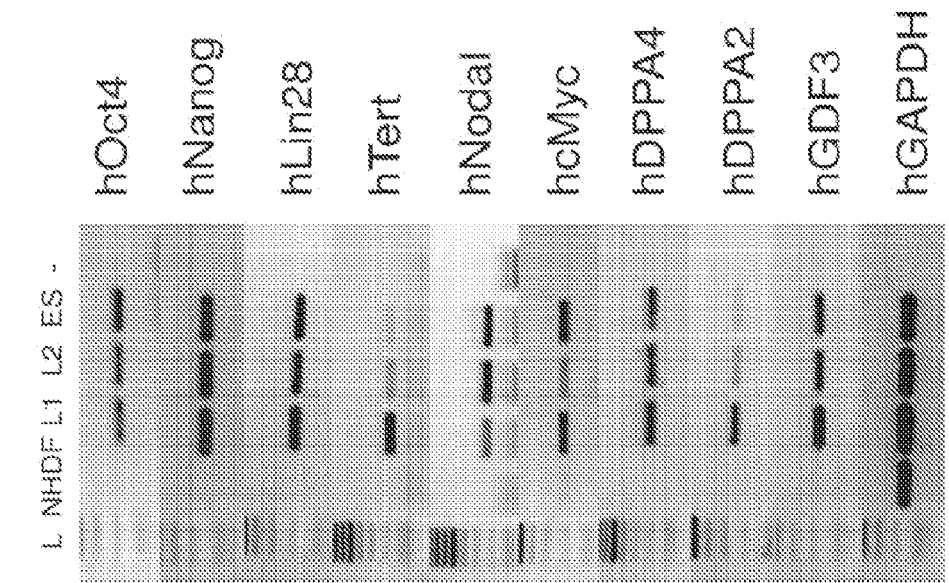
FIGS. 7A-B. The iPS cell line L-1 is pluripotent. (a) Immunofluorescence analysis of L-1 and H9 cells demonstrates that morphology and expression of several hES cell markers are similar in the two cell lines. (b) Gene expression patterns were compared between parental fibroblasts (NHDF), two iPS lines derived from NHDF cells (L1, L2) and the hES H9 cell line. Genes specific for pluripotent stem cells were expressed in common for iPS and ES cells, and differ from NHDF parental cells.
Figure 7A:
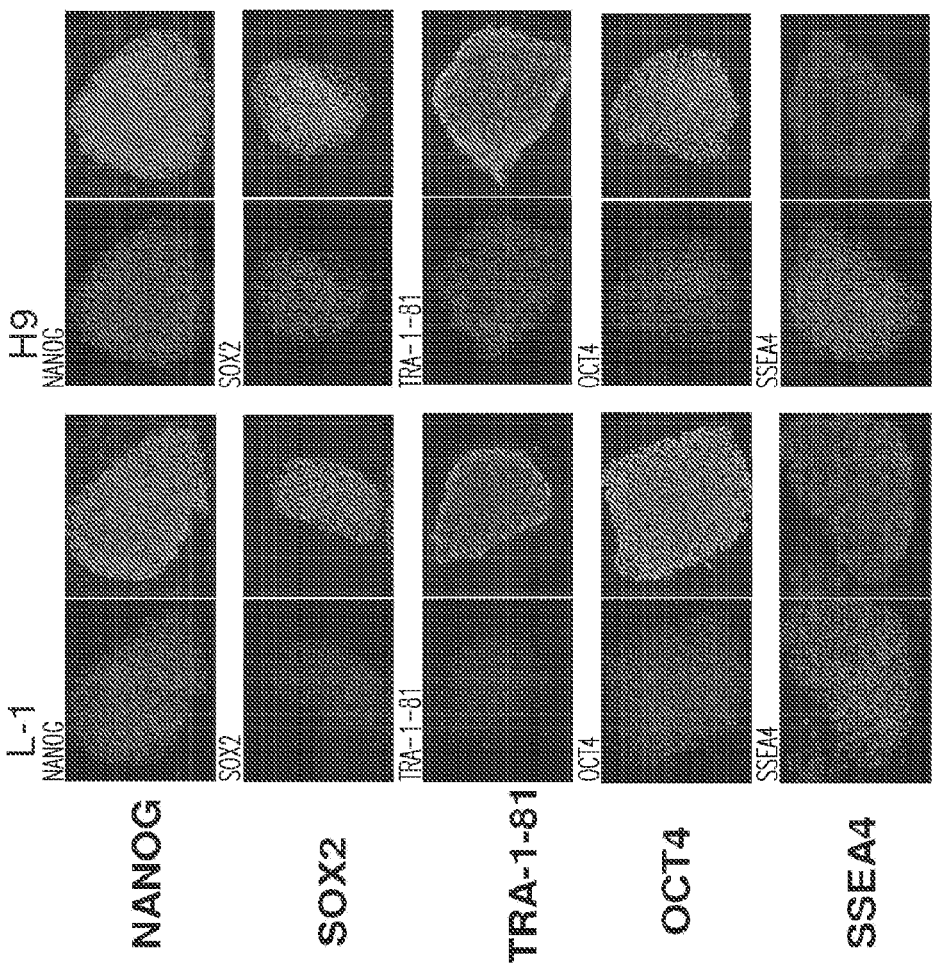
Figure 8A:
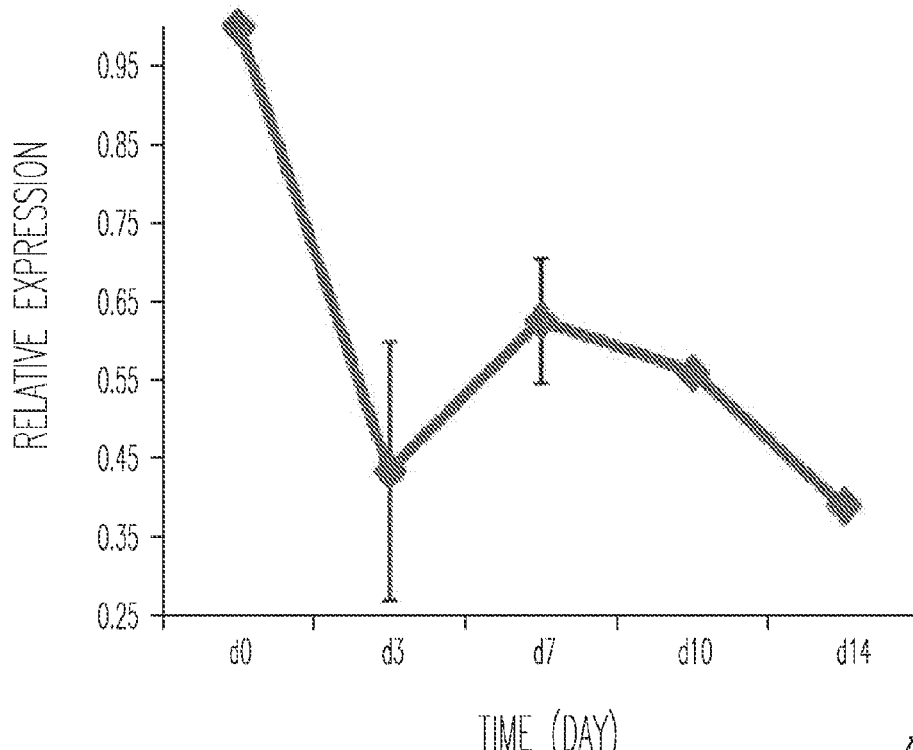
FIG. 8. The iPS cell line L-1 is pluripotent. L-1 cells were differentiated in suspension culture by EB (embryoid body) formation for two weeks. Quantitative PCR was performed, demonstrating that the L-1 cells differentiated into representative tissues of the three germ layers: Oct4, undifferentiated pluripotent cells; VE Cadherin, mesoderm; NCAM, ectoderm; AFP, endoderm.
Figure 8B:
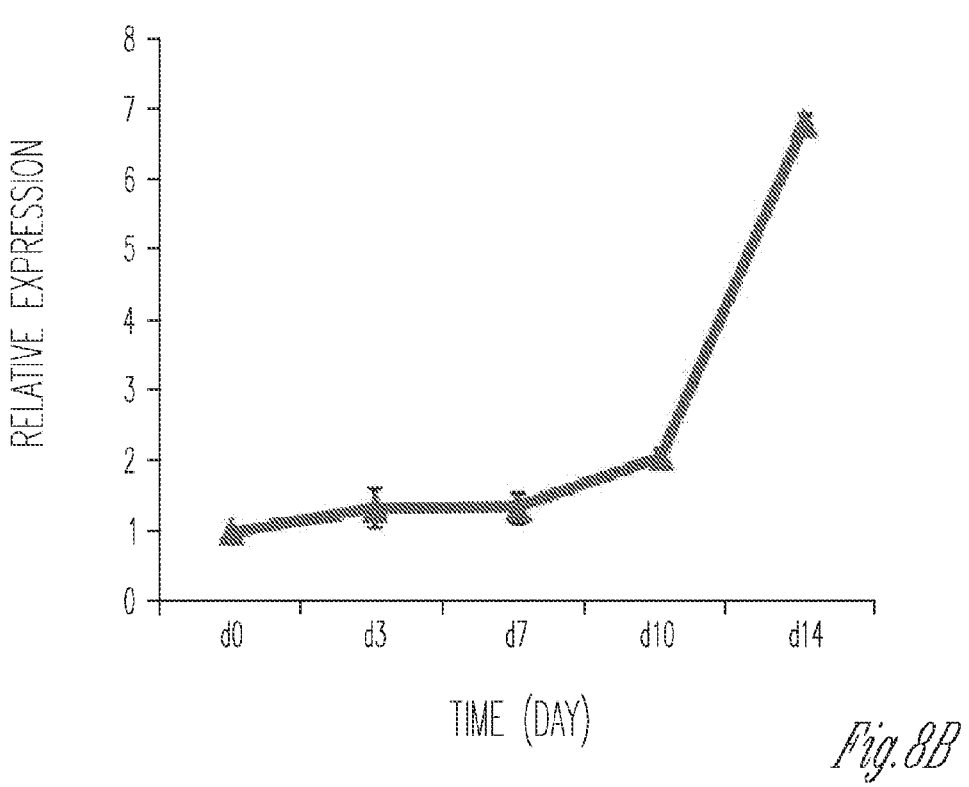
Figure 8C:
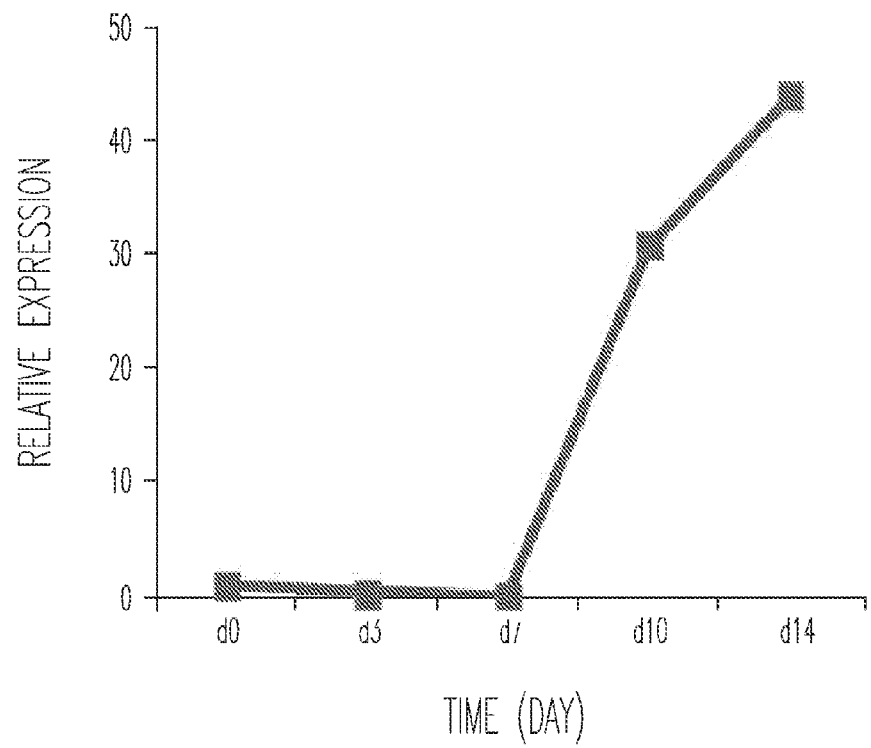
Figure 8D:
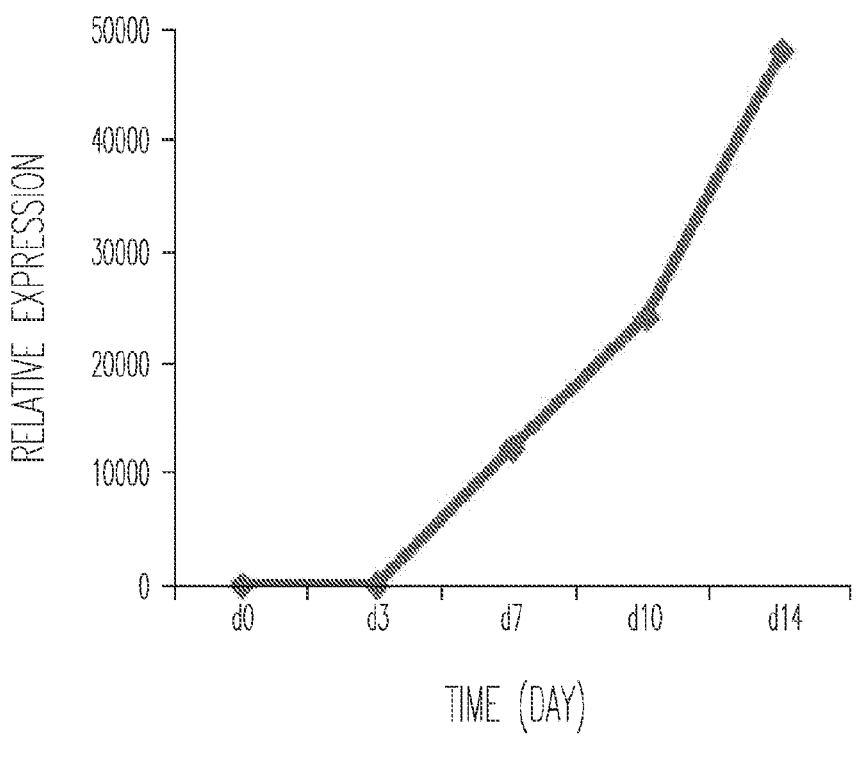

The four step protocol was used to direct differentiation of L-1 iPS cells. The L-1 cell line, derived by lentiviral infection of NHDFs, is karyotypically normal (data not shown), and has similar morphology and pluripotency marker gene expression to hES cells as shown by immunostaining (FIG. 7*a*). Two cell lines derived from NHDFs showed similar pluripotent marker gene expression to H9 hES cells (FIG. 7*b*). NHDF-derived lines (L-1 and L-2) and H9 cells express Oct4, Nanog and Lin28, as well as hTert, and several other pluripotency-associated genes in contrast to the expression of only hcMyc and the control marker GAPDH observed in the parent NHDF cells.

Figure 2A:
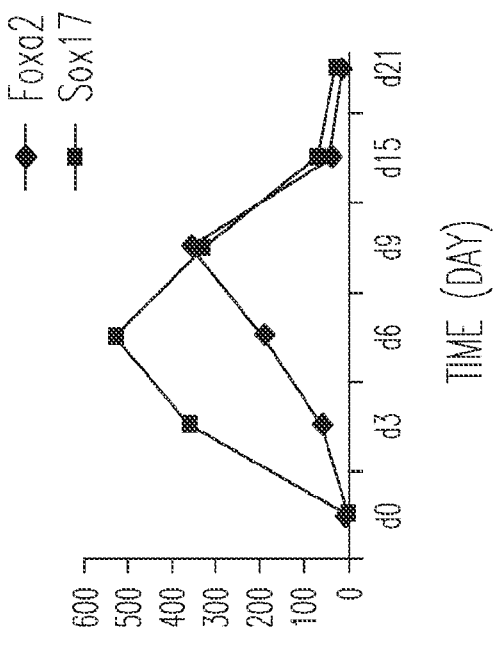
FIGS. 2A-D. Directed differentiation of iPS cells into insulin-producing cells progresses through developmental stages. L-1 iPS cells were directed to differentiate in EB suspension culture for 21 days with sequential cytokine stimulation to support differentiation into insulin-producing cells. Quantitative PCR analysis indicated that: (a) iPS cells differentiated into definitive endoderm, followed by pancreatic endoderm and (b) maturation of endocrine cells, in which insulin and related genes Rfx6 and glucokinase, markers of mature beta cells can be found in EB cultures. (c) Immunostaining of specific pancreatic marker proteins (pdx-1, insulin) in iPS derived cells at stage 4. (d) C-peptide secreted by iPS-derived cells was measured in 24-hour conditioned medium from undifferentiated (day 0), day 15, and day 21 cultured cells. C-peptide was measured by ELISA assay, and is used to estimate the amount of insulin secretion.
Figure 2A:
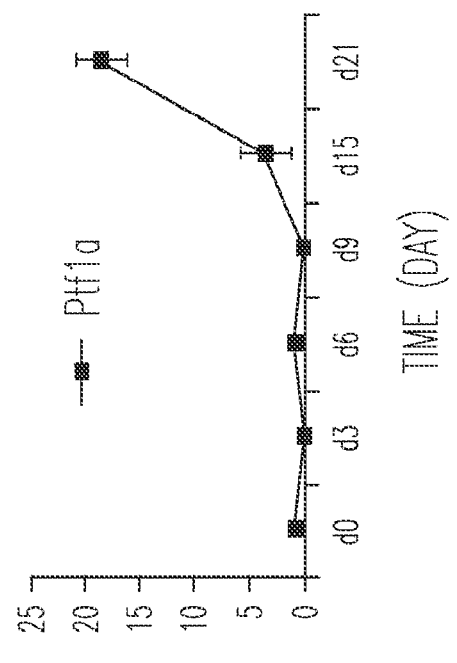
Figure 2A:
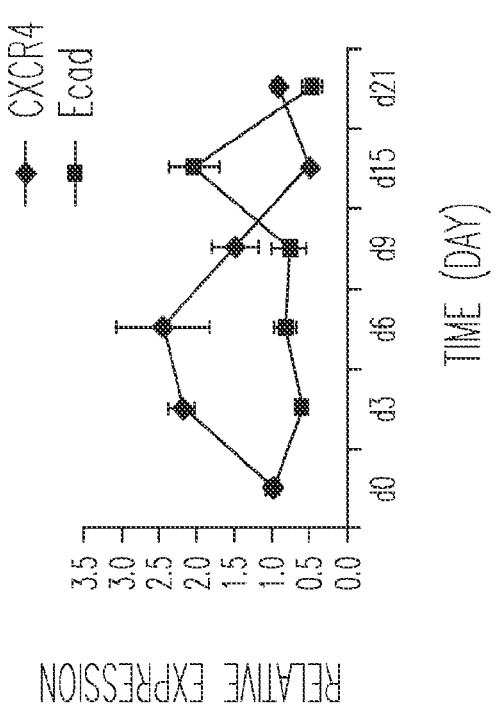
Figure 2A:
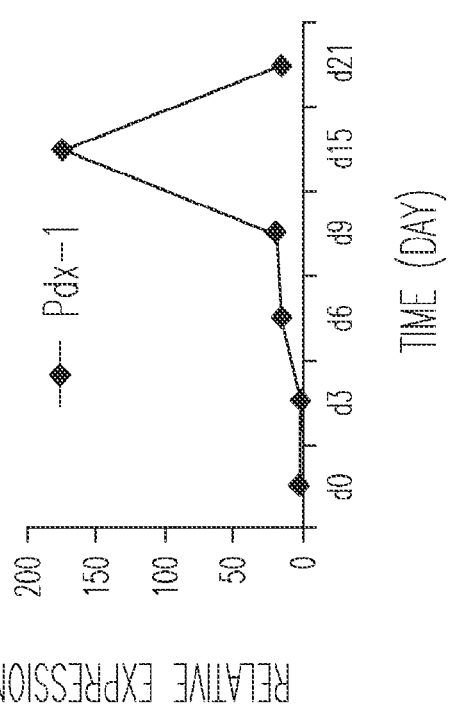
Figure 2B:
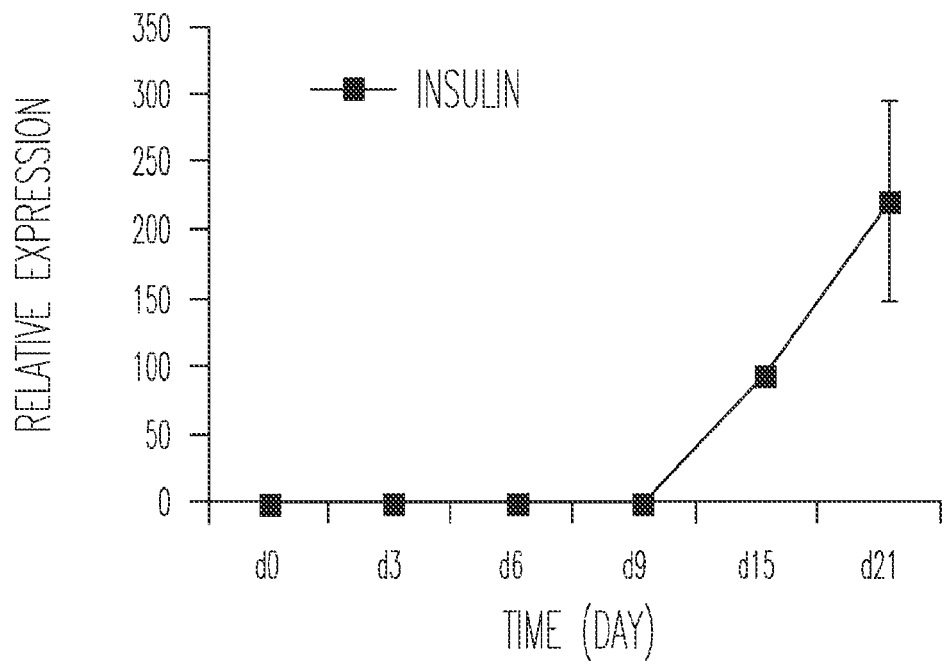
Figure 2B:
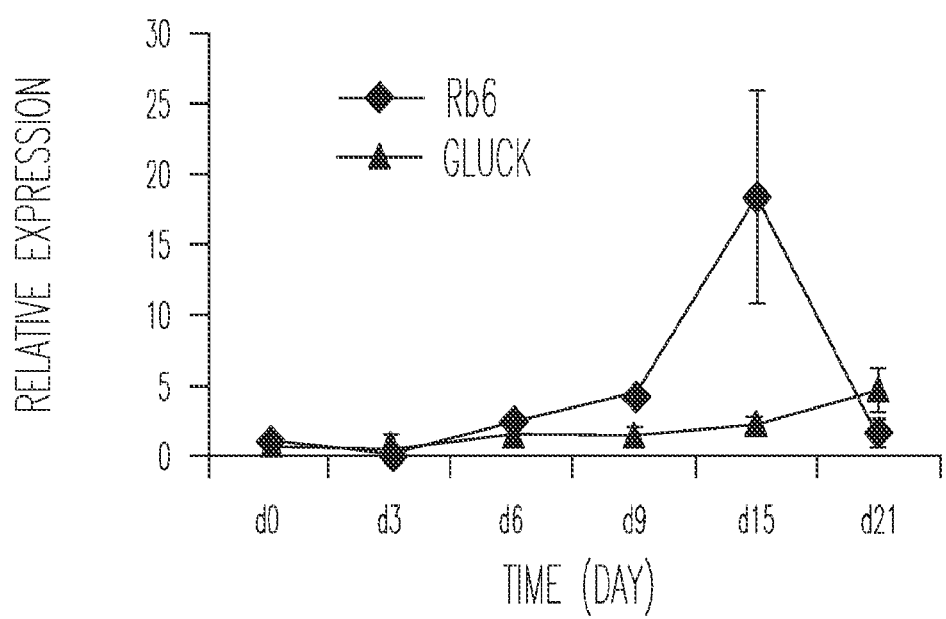
Figure 2C:
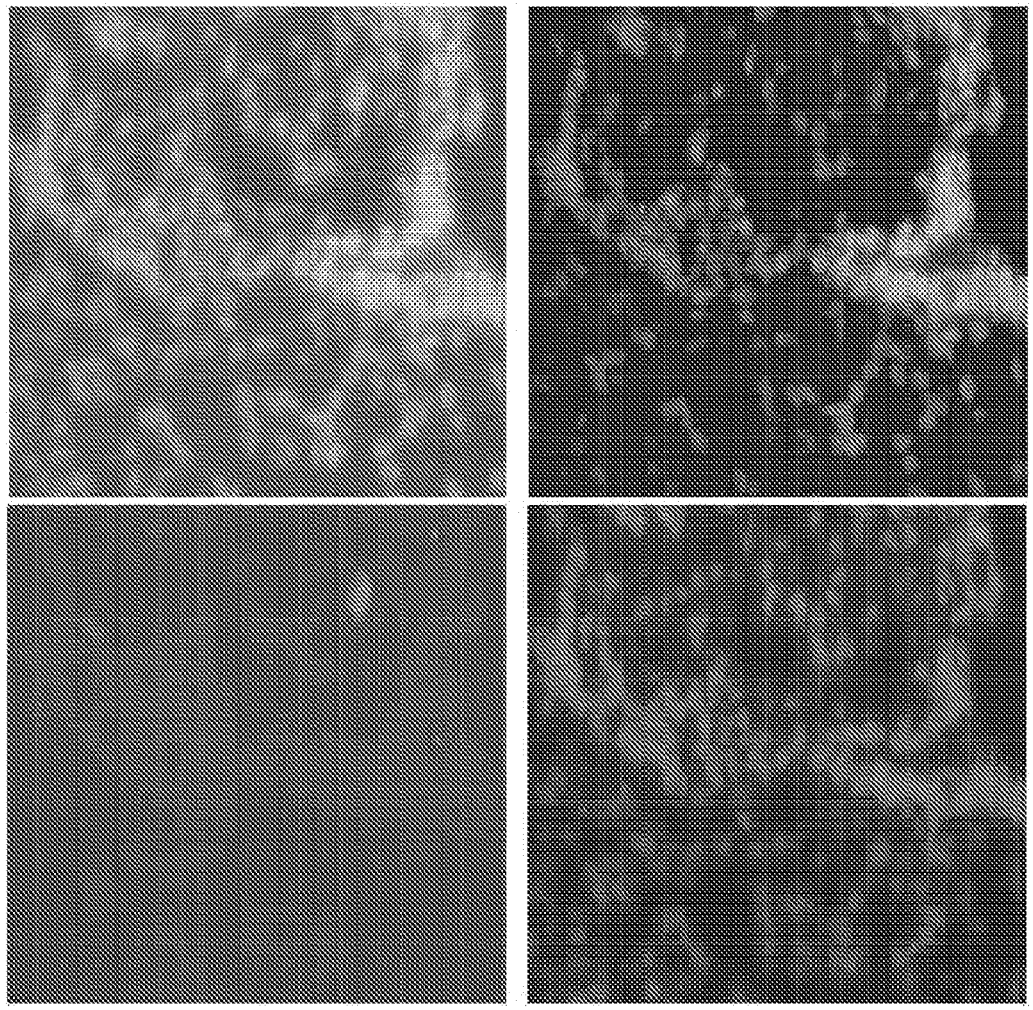
Figure 2D:
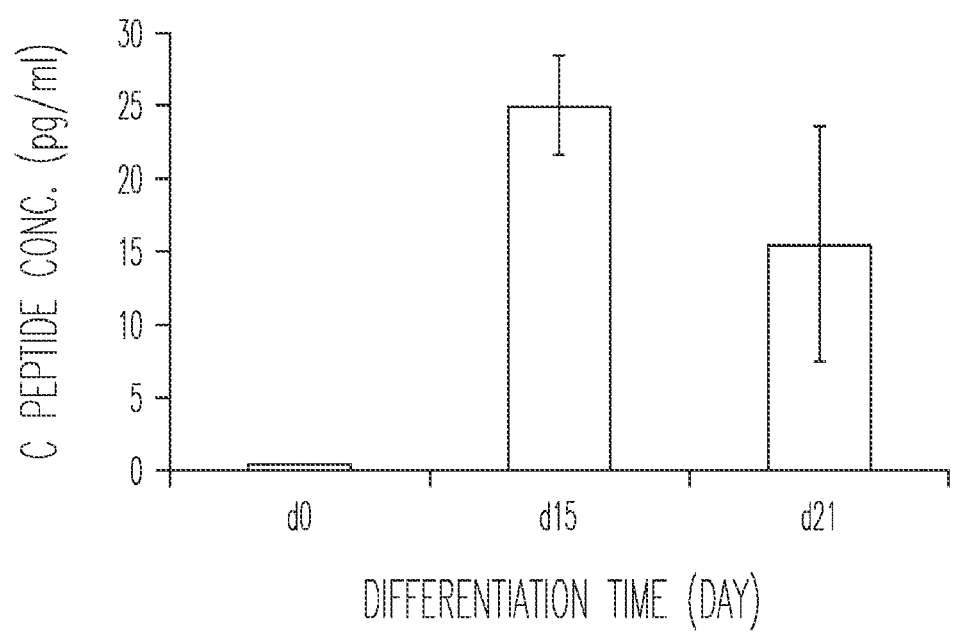

To demonstrate the pluripotency of the L-1 iPS line in vitro, unstimulated differentiation to representative cell types of the three germ cell layers was assessed (FIG. 8). The differentiation protocol developed for hES cells was applied to the L-1 cells. Embryoid Body cultures were established for 21 days with sequential cytokine stimulation (see Table 1). The L-1 cells were shown to differentiate into beta-like cells with the capacity for insulin secretion after maturation through the differentiation steps previously observed during culture of H-9 cells, consistent with normal pancreatic development (FIG. 2*a*). qPCR analysis for stage-specific markers showed sequential differentiation of the L-1 cells into endoderm, definitive endoderm, and then to pancreatic endoderm. High levels of the endodermal markers, CXCR4 and ECadherin, were detected within the first week. Immediately thereafter, definitive endodermal markers, Foxa2 and Sox17 were expressed at peak levels. Finally, the pancreatic endodermal markers Pdx-1 and Ptf1a were detected in the last week of differentiation. Markers related to mature beta cells and insulin secretion peaked in a similar time frame (FIG. 2*b*). Since pancreatic precursors transiently express Pdx-1 in vivo, followed by re-expression in mature insulin-producing beta cells, the expression of Pdx-1 and insulin was examined by immunostaining of cross-sections of EBs at day 21 (FIG. 2*c*). Examination of the cross-sections shows that no single cell expressed both of these markers, suggesting that precursors and immature insulin-producing cells, but not mature beta cells were present in these cultures. However, differentiated L-1 cells were actively secreting insulin, as measured by ELISA assay to detect human C-peptide concentration in the supernatant at different time points. The level of C-peptide was below the threshold of detection in undifferentiated day 0 L-1 cells. C-peptide secretion was detected in the medium of later stage cells beginning at day 15 of culture, suggesting that beta-like cells were present.

Figure 3A:
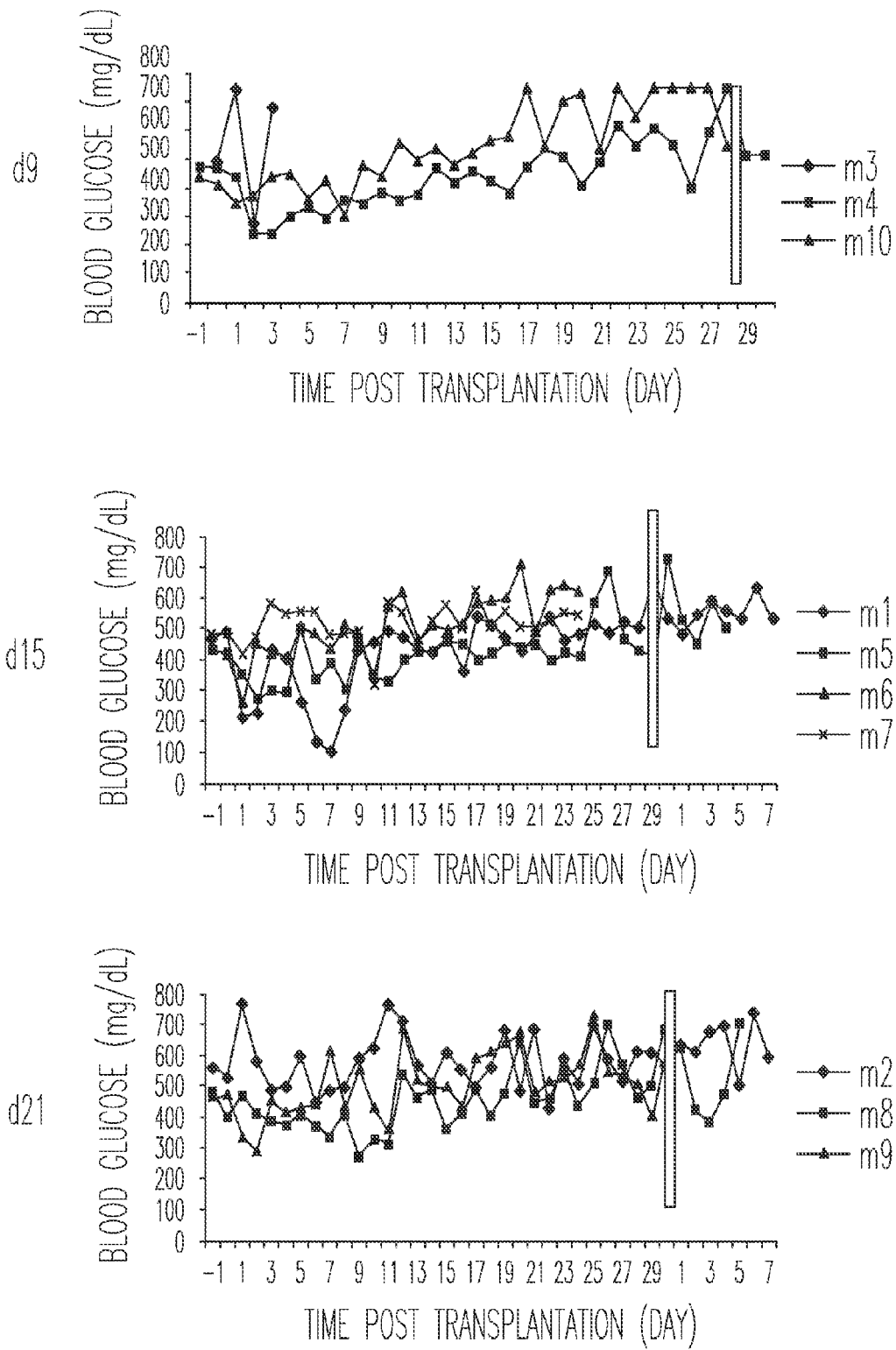
FIGS. 3A-B. Transplantation of induced L-1 iPS cells partially ameliorates diabetic symptoms. Changes in (a) blood glucose levels and (b) body weight were monitored daily in STZ-treated diabetic mice transplanted under the kidney capsule with cells differentiated for 9, 15 and 21 days. The solid vertical line indicates the time of graft removal. Mice were monitored for an additional 7 days to observe glucose levels and weight loss. After graft explant, weight loss was observed, suggesting that grafted iPS derived cells improved glycemic control.
Figure 3B:
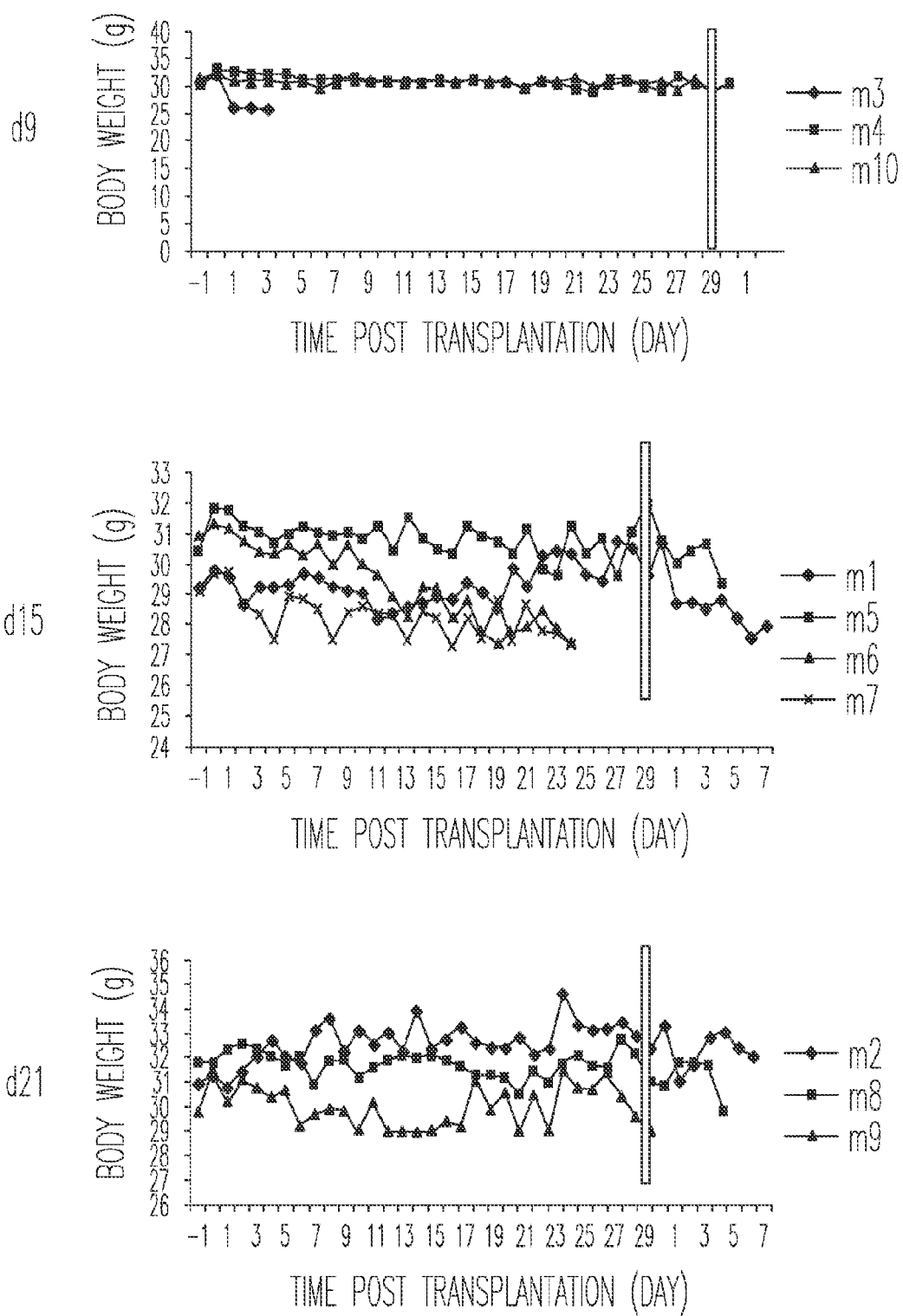
Figure 4:
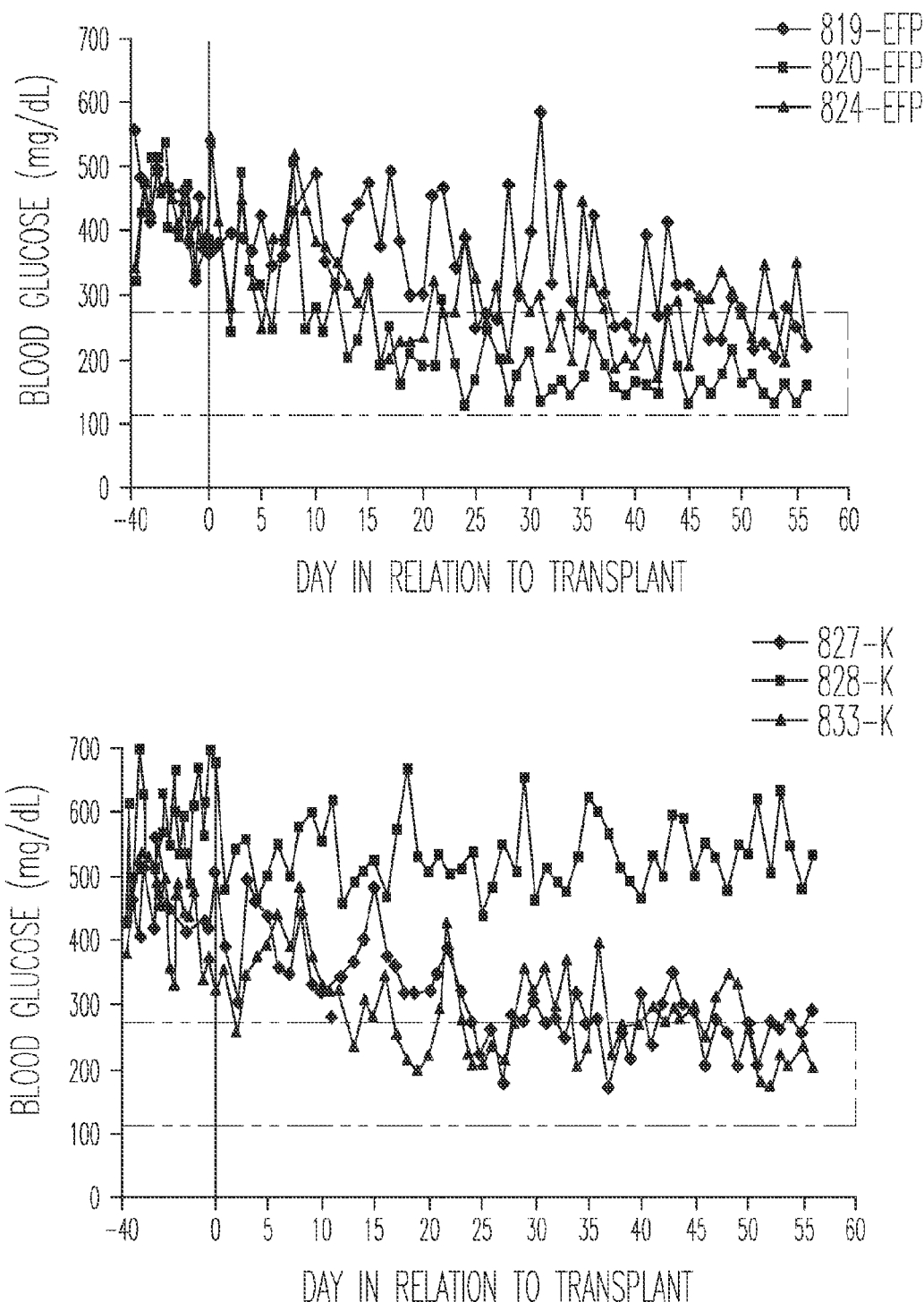
FIG. 4. Differentiated iPS cells reverse diabetes in mice. Day 15 differentiated iPS cultures (3-8×10$^6$ cells) were placed under the kidney capsule (K) or in the epididymal fat pad (EFP) of STZ-induced diabetic nude mice (n=6). After transplantation, daily insulin injections were administered until blood glucose levels were below 350 mg/dL. All glucose levels are non-fasting. The blood glucose level comparison between the pre (from day −40 to day 0) and post transplantation (from day 0 to day 56) period for each mouse. The shaded area shows the average normal blood glucose level plus and minus two standard derivations in the mice.

While a few groups have been successful in generating iPS-derived cells with evidence of insulin production in vitro, the function of these cell lines has not been tested in vivo. Differentiated L-1 cells generated in the studies above were transplanted under the kidney capsule of streptozotocin (STZ) induced diabetic mice to test the ability of the beta-like cells to reduce hyperglycemia and reverse the diabetic state. Initially, cells from different time points were transplanted to determine the optimal timing and cell doses. In this initial phase, insulin injections were withdrawn at the time of transplantation. Blood glucose levels and body weights of STZ-treated mice were measured daily over a three week period after transplantation (FIGS. 3*a* and 3*b*). Cells transplanted at day 15 of EB culture showed transient reduction of glucose levels to normoglycemia, and levels over the three weeks, though elevated, were maintained similar to those with daily insulin injections prior to transplantation. No exogenous insulin was given after graft explant, body weights decreased, suggesting the differentiated L-1 graft contributed to glycemic control and metabolic stability prior to explant.

Figure 5B:
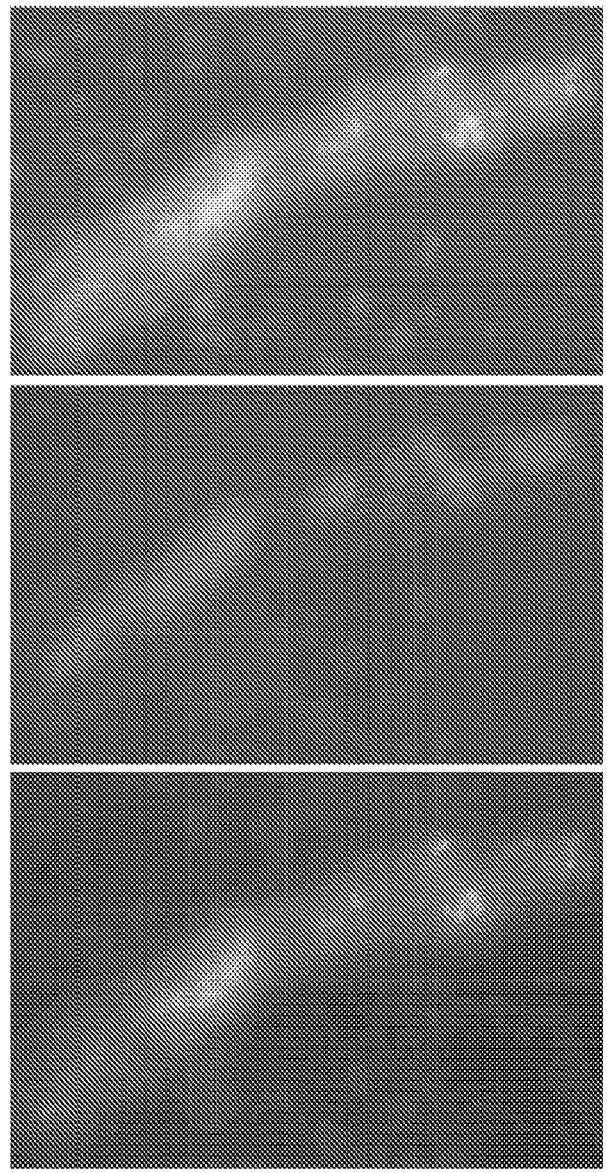
FIGS. 5A-B. iPS-derived grafts contain insulin-producing cells. Grafts were removed from mice 56 days after transplantation for insulin expression analysis. Grafts under the kidney capsule (g) were separated from kidney tissue (k) and grafts in the epididymal fat pad (e) were analyzed intact. (a) Quantitative RT-PCR was performed for insulin and Rfx6 expression in excised grafts. G, GAPDH; I, Insulin; R, Rfx6; hfp, human fetal pancreas. (b) Grafts were sectioned and stained for human pro-insulin and pdx-1, markers of mature beta cells. Clusters of cells co-expressing pdx-1 and pro-insulin are present in the grafts in addition to pro-insulin expressing cells that are negative for pdx-1.
Figure 5A:
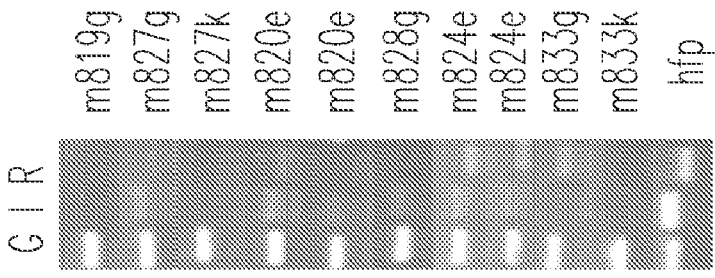

In the second phase of the study, mice were maintained after transplantation with daily insulin administration until glucose was measured to be lower than 350 mg/dL, a level consistent with the survival of the mouse. Cultures of differentiated cells were grown in stirred bioreactors to facilitate transplantation of larger cell doses, and in larger numbers of mice, using the same differentiation scheme. Differentiated L-1 cells ($4$-$8\times10^6$) were transplanted either under the kidney capsule, or into the epidermal fat pad (EFP). Blood glucose levels and body weights were measured daily (FIGS. 4*a* and 4*b*). In this experiment, transplantation of differentiated iPS cells reversed diabetes to below the target level of 350 mg/dL in five of six mice tested, yielding stable glucose levels for more than 3 weeks, although the levels varied among the mice. Human C-peptide levels were measured in a human specific radioimmunoassay (RIA) to ascertain whether insulin secretion was human graft-dependent or produced by the murine host. Human C-peptide levels were measured in a human specific radioimmunoassay (RIA) to ascertain whether insulin secretion was human graft-dependent or produced by the murine host. Human C-peptide was detected in at least one of the six mice tested, supporting the conclusion that insulin production from the graft was responsible for reduction of glucose levels and maintenance of body weight. The graft was then removed and immunostaining for pdx-1 and proinsulin was performed. FIG. 5 shows that there was co-expression of both of these markers in cells from transplanted grafts supporting the conclusion that mature beta cells formed in vivo. This correlated with normalization of glucose in this mouse. No insulin-positive cells were detected in the graft from the mouse with the highest glucose levels, although qPCR analysis demonstrated insulin expression in the grafts.

These studies establish the feasibility of differentiating iPS cells derived from human dermal fibroblasts to insulin-producing cells in vitro using a novel four-step protocol. The beta-like cells secrete biologically relevant levels of insulin when transplanted in STZ-treated diabetic mice, demonstrated by their capacity to reverse diabetes. The observations, in conjunction with ES cell and in vitro iPS studies of others (Shim (2007); Jiang et al (2007); Philips et al. (2007); D'Amour et al. (2005); D'Amour et al. (2006); Kroon et al. (2008); Zhang et al. (2009); Tateishi et al. (2008); Maehra et al. (2009)), support the hypothesis that differentiation of pluripotent cells in vitro faithfully recapitulates in vivo pancreatic developmental patterns (Habener et al. (2005) and Jensen (2004)). Insulin secretion was observed at later stages of differentiation, but glucose-stimulated insulin secretion was not observed either in the cultures analyzed in this study, or in studies with ES cells. The glucose insensitivity of insulin-producing cells in late stage iPS cultures is similar to the phenotype of fetal pancreatic islet cells as the progression to glucose-responsive beta cells occurs after birth. Additional evidence that precursors, but not beta cells were present in EBs prior to transplantation comes from the lack of expression of pdx-1 in insulin producing cells. Immunohistochemical data showed that insulin-producing cells in EBs at the time of transplantation did not co-express pdx-1, as would be expected in mature beta cells. These observations support the interpretation that mature beta cells were not present at day 15 of differentiation even though C-peptide was present in the supernatant of these cultures. However, since insulin/pdx-1 co-expressing cells were present in the grafts after excision, further maturation could after transplantation. The transplantation of mature beta cells is not required to achieve glucose regulation by less mature cells in vivo, since glucose levels were significantly reduced in engrafted mice as early as day 12 after transplant.

Methods of differentiation previously used to generate insulin-producing cells have been complicated, requiring multiple steps and the addition of many individually added cytokines, without significant expansion of cell numbers (D'Amour et al. (2006)). Simplified differentiation schemes such as the methods used here have significant advantages, requiring fewer individual recombinant factors which will facilitate standardization and reduce costs of the scale-up of cultured cells for transplantation. Further, the culture of cell clusters like EBs in suspension is amenable to larger scale bioreactors. In all of the previous studies, inhibition of Shh signaling from definitive endoderm, a step required for the specification of pancreas, was achieved by the addition of cyclopamine, a toxic chemical. In this study, similar results were achieved by the addition of an inhibiting antibody that blocks Shh signaling without associated toxicity.

In summary, it is reported herein for the first time, a robust and scalable iPS differentiation method to generate insulin-producing cells that rescue diabetes. This study demonstrates that patient-specific cells may be useful both as a model of human pancreatic development for investigating the events leading to type 1 diabetes, and for the generation of therapies that will provide sufficient islet replacement cells for the treatment of type 1 diabetes.

Islet replacement therapy for type 1 diabetes is a promising approach for restoring insulin-producing beta cells; however, broad implementation of this strategy is currently not feasible due to the scarcity of donor tissues. A potential solution to this problem would be the directed differentiation of human pluripotent stem cells, including embryonic stem (ES) cells and induced pluripotent stem (iPS) cells into insulin-producing cells. While others have succeeded in deriving cells that secrete insulin, protocols have been complex and therefore not optimal for clinical translation. A streamlined, broadly applicable four-step differentiation process has been developed demonstrating that hES cells and human iPS cells from dermal fibroblast cells generate insulin-producing cells. Further, the biological functionality of these differentiated iPS cells was validated by transplantation into diabetic mice and subsequent reversal of diabetes in vivo. Thus, the study provides the first direct in vivo evidence that insulin-producing cells can be generated from iPS cells using a robust process.

Example II

Bioreactor Cultured Human iPS Cell Derived Pancreatic Progenitors Enhance Diabetic Mice Survival Materials and Methods Cell culture: iPS cell lines were cultured in iPS medium (DMEM/F12 medium containing 20% knockout serum replacement, 0.1 mM nonessential amino acids, L-glutamine, 0.1 mM β-mercaptoethanol and 100 ng/ml basic fibroblast growth factor). Cultures were maintained on irradiated primary (MEF) feeders and passaged enzymatically using 10 µg/ml collagenase IV (Invitrogen).

Directed differentiation: Directed differentiation was achieved using embryoid body (EB) formation (Embryoid Body (EB) culture is used to examine the differentiation potential of the embryonic stem (ES) cell line. The cells are grown using low-attachment dishes in the presence of complete growth medium. This process induces differentiation, permits suspension culture, and causes the cells to form aggregates). The differentiation was initiated by harvesting human iPS colonies using collagenase and shearing with a serological pipet. Differentiation was carried out in suspension culture of EBs using a 4-step process in differentiation medium (DMEM supplemented with 2% FBS, 1 mM L-glutamine, 0.1 mM nonessential amino acids, 0.1 mM β-mercaptoethanol) with the following steps: Stage 1: from day 0 to day 3, the culture was supplemented with 100 ng/ml Activin A and 50 ng/ml Wnt3a. Stage 2: From day 3 to day 9, the medium was supplemented 2.5 mg/ml anti-human Shh in addition to Activin A and Wnt3a. Stage 3: from day 9 to day 15, the medium was supplemented with 50 ng/ml hEGF and 50 ng/ml heparin sulfate. Stage 4: from day 15 to day 21, the medium contained 50 ng/ml hGDF-11, 50 ng/ml hBetacellulin and 10 nM Exendin. All cytokines except Exendin (Sigma) were from R&D Systems. The stimulation protocol is as shown in FIG. 1. The medium was replaced every 3 days. Samples of EBs were harvested every 3 days for analysis to identify specific cell populations, and for cell counts and viability assays. Differentiation was conducted in the following suspension cultures: 1) 24-well Ultra-low attachment plate or 10 cm Petri dishes (Corning) with 1 or 10 ml medium for static culture; 2) 100 ml stirred bioreactor (Wheaton Science) large scale culture with 70 rpm rotation by a low speed stirrer (Wheaton Science). All incubations were carried out in a 5% $CO_2$ incubator at 37° C.

Biochemical Assays: EB samples were taken from the suspension cultures at the different time points and were extensively washed with PBS 3 times. Cells were then lysed in different buffers from DNA (DNAeasy blood & tissue kit, QIAGEN) and protein assay kits and follow the manufacturer's instructions for the assays (BCA protein assay kit, thermo Scientific).

EB number, size, cell density and viability: Samples from all culture systems were collected, EB sizes from different culture systems were compared using inverted light microscopy (ZEISS, Axiovert 200M). To count cells, samples of EBs were treated with Accumax (Sigma) at 37° C. for 30 minutes and counted using Trypan blue dye exclusion on a hemacytometer.

RNA Extraction and gene expression analysis: Total RNA was extracted from cell samples using the RNeasy Micro kit (Qiagen) according to the protocol provided in the kit and 0.5-5 µg of the extracted total RNA was used in reverse transcription to synthesize cDNA using the SuperScript III First-stand Synthesis System for RT-PCR kit (Invitrogen). Quantitative PCR (qPCR) was carried out with cDNA using SYBR Green (Applied Biosystems) on an Eppendorf Mastercycler (realplex2). Primers used for amplification are listed in Table 2.

TABLE 2

Primer sets

| Gene marker | Sets | sequence | |
|---|---|---|---|
| GAPDH | F | GAGTCAACGGATTTGGTCGT | (SEQ ID NO: 1) |
| | R | GACAAGCTTCCCGTTCTCAG | (SEQ ID NO: 2) |
| Sox17 | F | CGCACGGAATTTGAACAGTA | (SEQ ID NO: 3) |
| | R | GGATCAGGGACCTGTCACAC | (SEQ ID NO: 4) |
| Foxa2 | F | ATTGCTGGTCGTTTGTTGTG | (SEQ ID NO: 5) |
| | R | TACGTGTTCATGCCGTTCAT | (SEQ ID NO: 6) |
| Pdx-1 | F | CATTGGAAGGCTCCCTAACACA (SEQ ID NO: 7) | |
| | R | GGCATCAATTTCACGGGATC | (SEQ ID NO: 8) |
| Insulin | F | CTACCTAGTGTGCGGGGAAC | (SEQ ID NO: 9) |
| | R | GCTGGTAGAGGGAGCAGATG | (SEQ ID NO: 10) |

Transplantation of differentiated L-1 cells into mice: Mice were socially housed and participated in a complete enrichment program. Dietary enrichment included provision of black oil sunflower seeds (Bio-Serv, Frenchtown, N.J.) and Enrich Mix (1922 Harlan Teklad, Madison, Wis.) daily. Environmental enrichment included a crawl ball, polycarbonate igloo, or paper hut.

Diabetes Induction in Nude Mice: Adult male nude mice, 29.7-33.5 grams, were obtained from the Charles River Laboratories (Wilmington, Mass., USA). Diabetes induction was accomplished using a single IP infusion of streptozotocin (STZ, Zanosar; Sicor Pharmaceuticals, Irvine, Calif., USA) 240 mg/kg bolus. Following the administration of STZ, animals were closely monitored for adverse events Animals received supportive hydration (1-3 ml normal saline IP) concomitantly and as clinically indicated post STZ injection. Blood glucose and weight were measured daily or as clinically indicated from STZ to the scheduled experimental endpoint. Blood glucose levels were measured by bleeding the tail vein. Mice with a blood glucose level >300 mg/dL for 2 consecutive days were considered diabetic, at which time insulin injections were initiated. In diabetic mice, 0.5U glargine (Lantus, Aventis, Parsippany, N.J.) was injected subcutaneously, daily or as clinically indicated, until beta cell transplant, or in some experiments until glucose levels were stabilized below 350 mg/dL. Blood collection, via tail or facial vein bleed, was performed approximately every 14 days for RIA analysis for human C-peptide using the Millipore human RIA kit according to the manufacturers instructions.

Transplant Under Renal Capsule of Nude Mice: Isoflurane was delivered via precision anesthetic vaporizer for anesthesia. After full aseptic preparation using Technicare surgical scrub (C are Tech Laboratories, St Louis, Mo.), the mouse was placed laterally on surgical field. Using a sterile dissecting forceps and scissors a 1 cm incision in the skin and peritoneum was created to expose the kidney. The kidney was gently externalized using palpation. A small nick (1-3 mm) to the kidney capsule was made and the collected differentiated iPS cells, approximately $1-2 \times 10^6$ cells or $3.5-5.5 \times 10^6$ cells were placed under the kidney capsule, using PE160 tubing attached to a Hamilton syringe. The kidney was reintroduced into the peritoneum, the muscle layer was approximated, and the skin layer was closed with absorbable suture. Analgesia was accomplished using ketoprofen 5 mg/kg SC a single dose pre-operatively, and as needed post operatively.

Transplant in Epididymal Fat Pad of Nude Mice: Isoflurane was delivered via precision anesthetic vaporizer for anesthesia. After full aseptic preparation using Technicare surgical scrub (C are Tech Laboratories, St Louis, Mo.), the mouse was placed dorsally on surgical field. Using a sterile dissecting forceps and scissors a 1 cm incision in the skin and fascia was created on the ventral midline in the groin area. The epididymal fad pad (EFP) was gently exposed and kept moist with physiologic saline. A purse string suture was used at the periphery of the EFP to create a pouch. Between 4 and $8 \times 10^6$ differentiated iPS cells were loaded into PE160 tubing, the PE tubing placed into the pouch, and cells were delivered to the EFP pouch. The purse string was ligated, closing the opening and marking site of implantation. The fascia and skin were closed with absorbable suture. Analgesia was accomplished using ketoprofen 5 mg/kg SC a single dose pre-operatively, and as needed post operatively.

Results

The Growth of Differentiated iPS Cell in Stirred Bioreactor Culture is Comparable with Static Culture and Provides for Large Scale Culture.

Figure 9A:
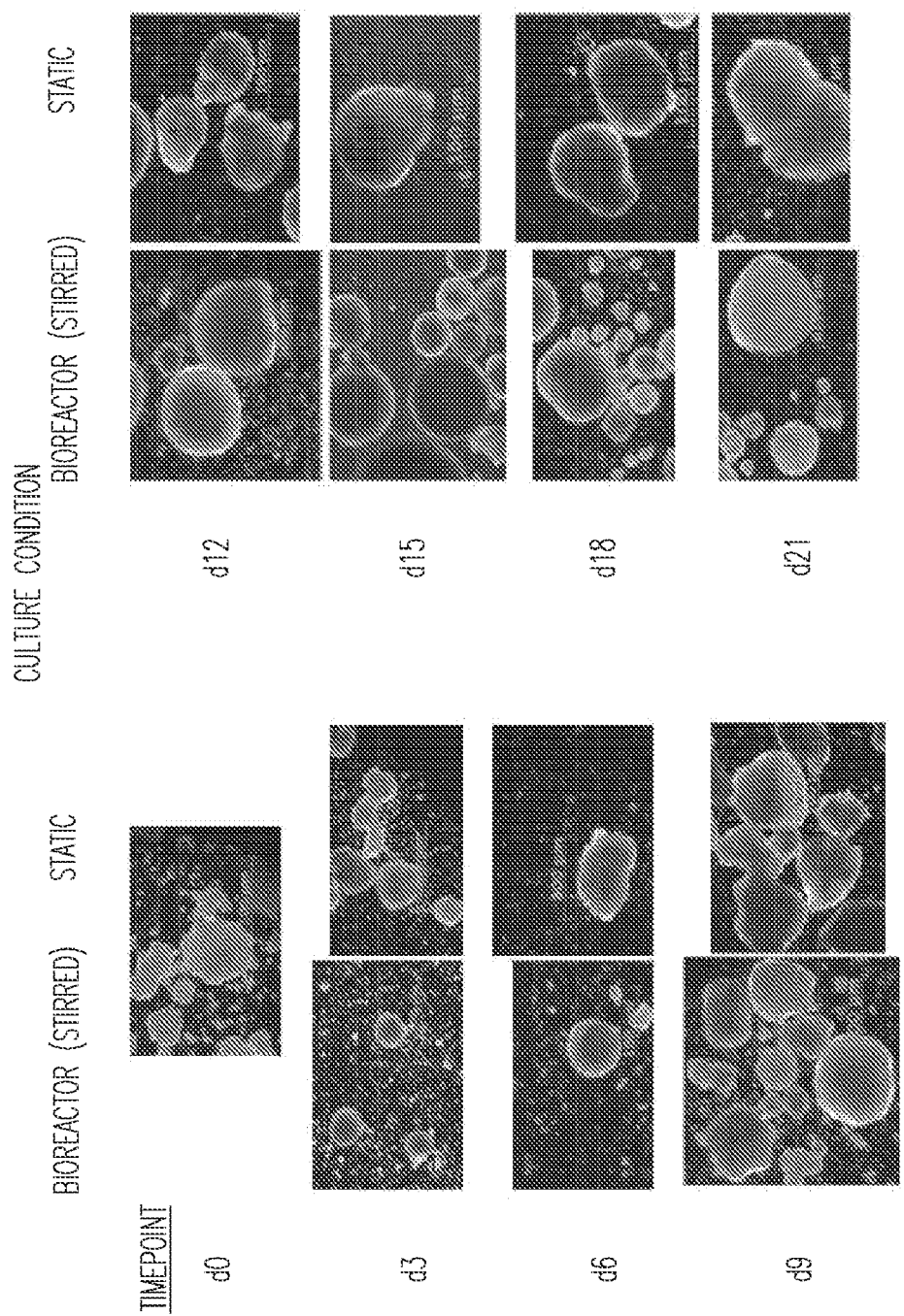
FIGS. 9A-G: Comparison of EB growth in small static and stirred bioreactor culture. (a) EB morphology at different time points of differentiation. (b) EB growth detected by cell density and viability. (c), (d), (e) EB growth determined by measurement of EB number and EB size. (f), (g) total DNA and protein amount static and stirred bioreactor culture were compared as an estimate of cell numbers.
Figure 9B:
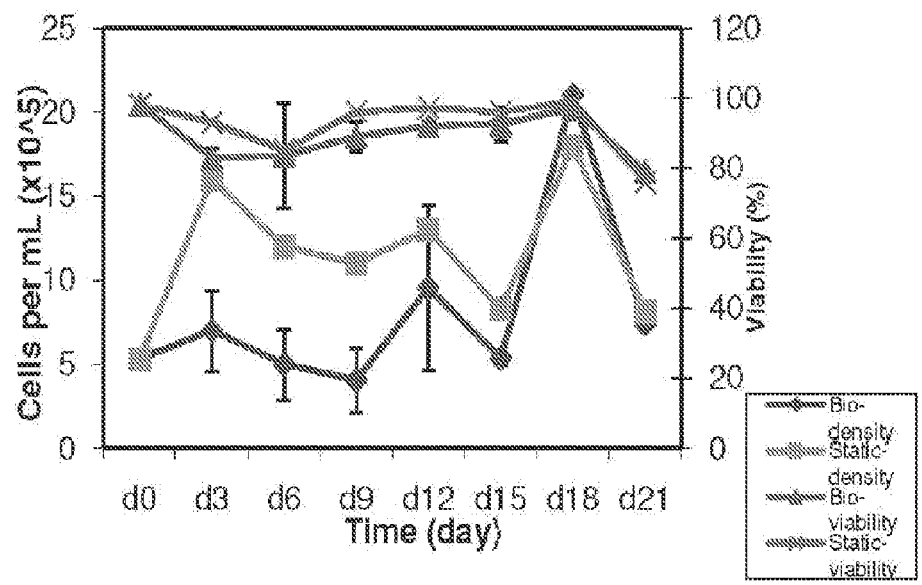
Figure 9C:
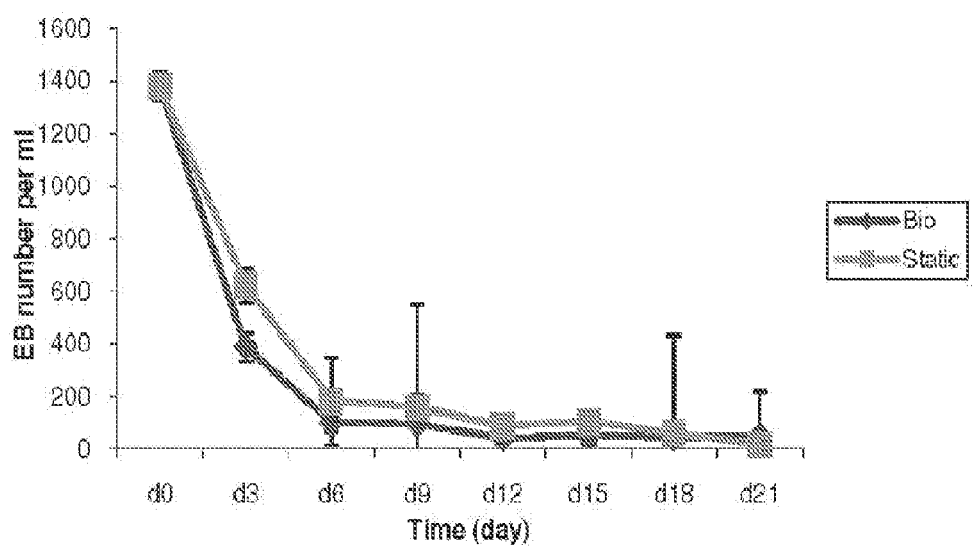
Figure 9D:
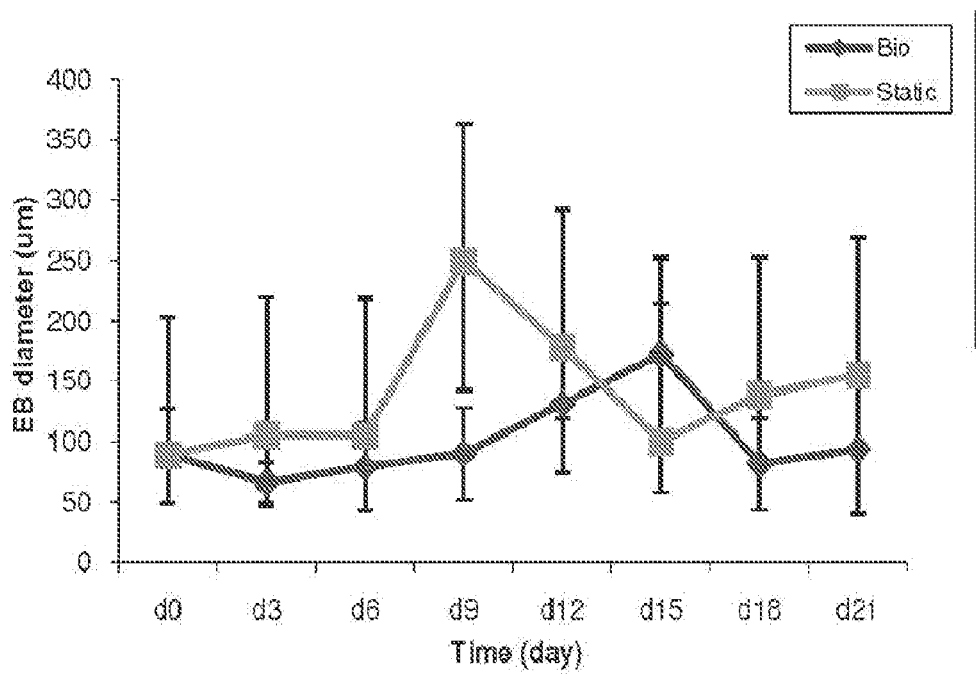
Figure 9E:
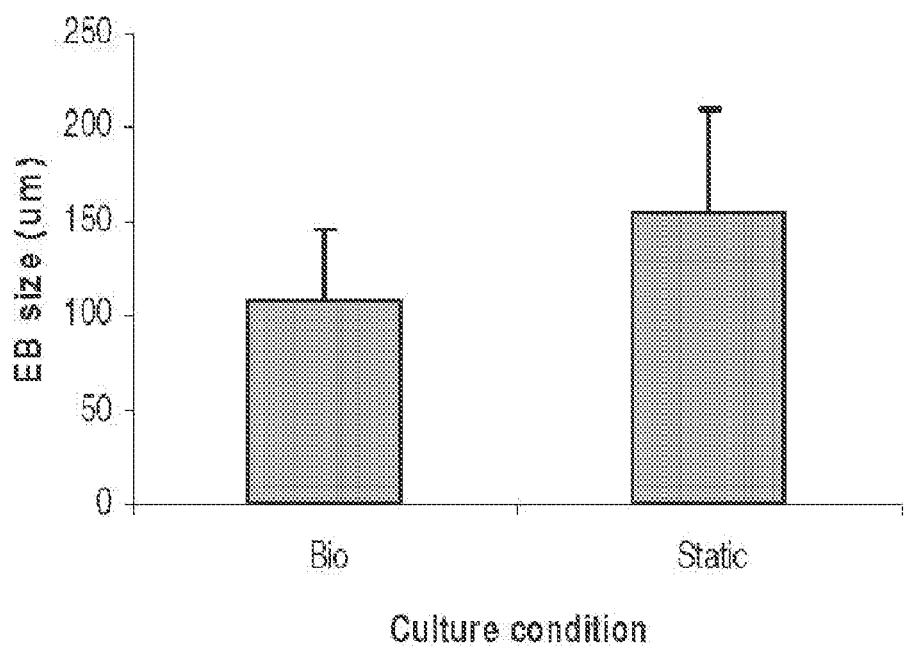
Figure 9F:
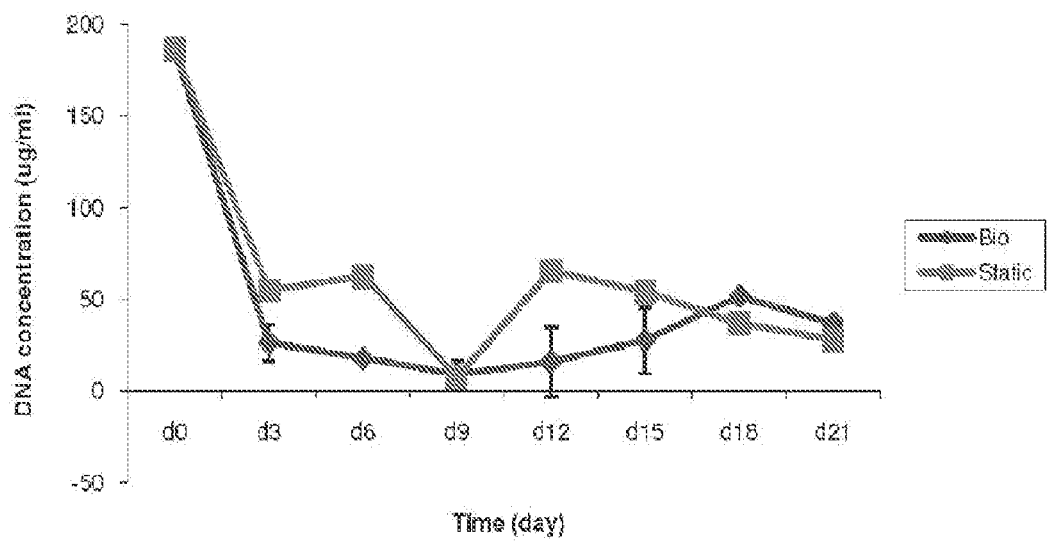
Figure 9G:
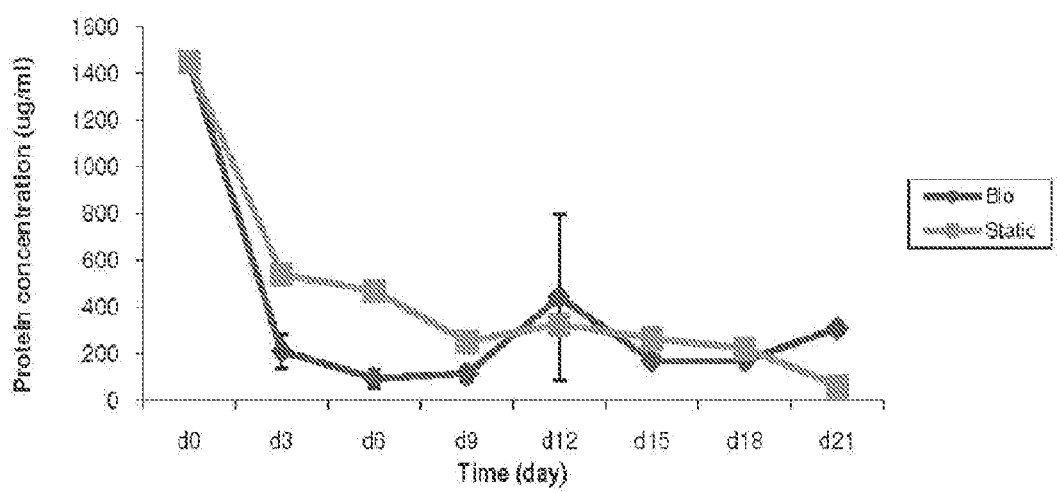
Figure 10A:
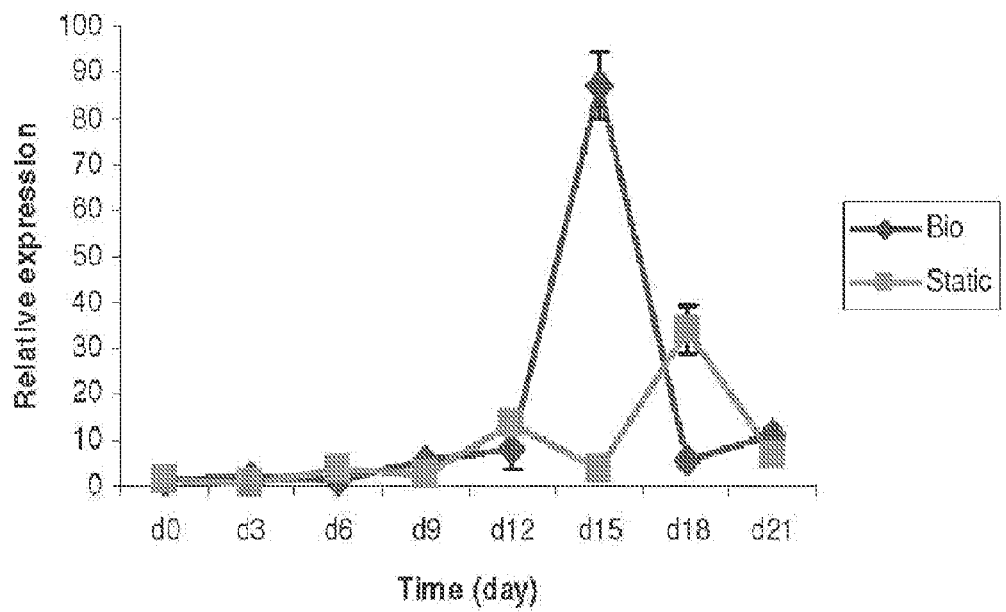
FIGS. 10A-H: Directed differentiation of iPS cells in stirred bioreactors exhibited similar development patterns as small-scale static cultures. (a) Comparison of each stage gene expression was performed by qPCR. Gene expression in individual samples were normalized to the GAPDH gene expression. The value of undifferentiated (d0) iPS cells was set as 1. (b) Summary of definitive endoderm and pancreatic endoderm gene expression in multiple bioreactor and static cultures. Gene expression from static cultures was set as 1 for each time point.
Figure 10B:
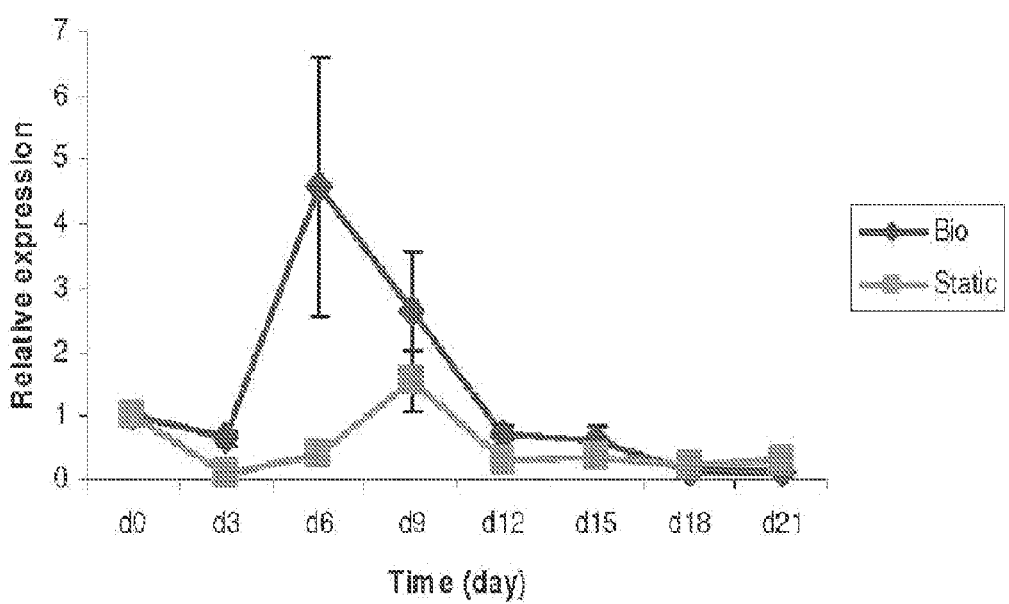
Figure 10C:
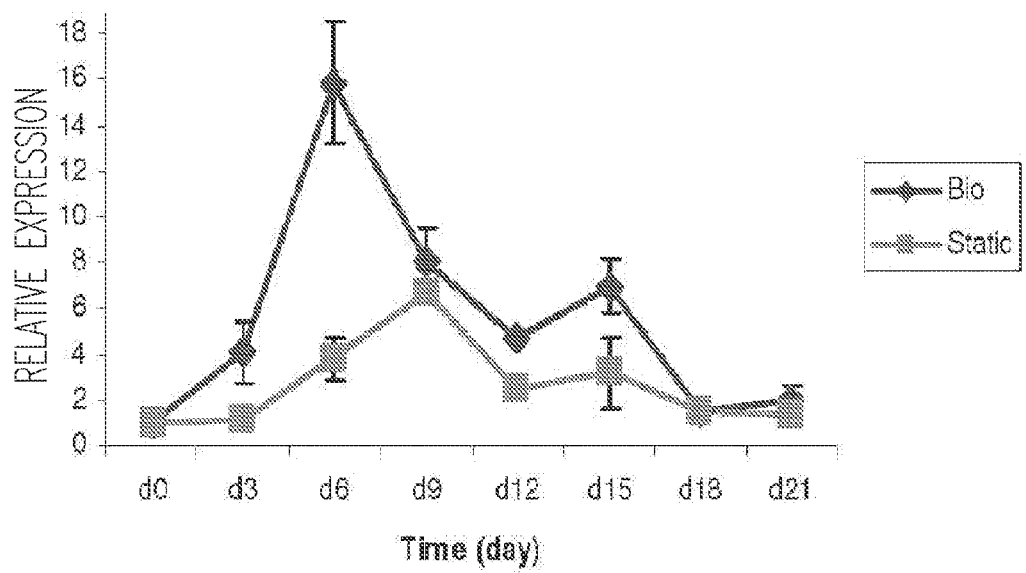
Figure 10D:
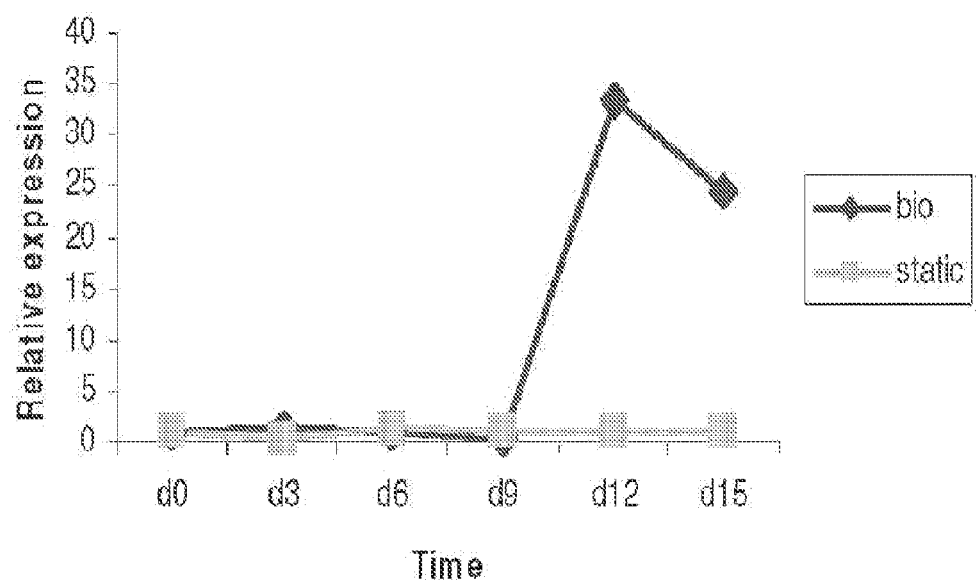
Figure 10E:
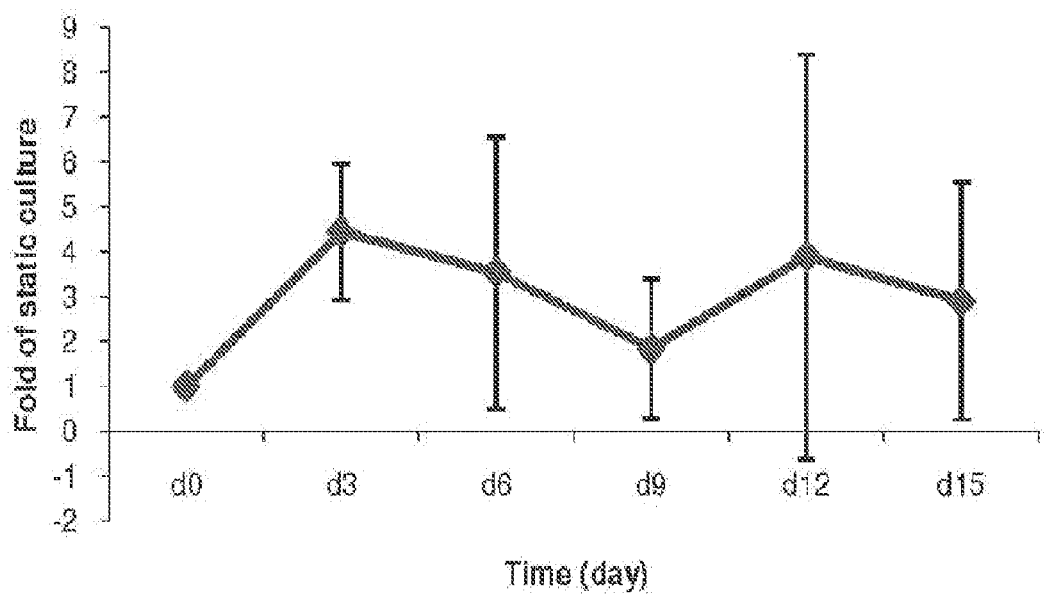
Figure 10F:
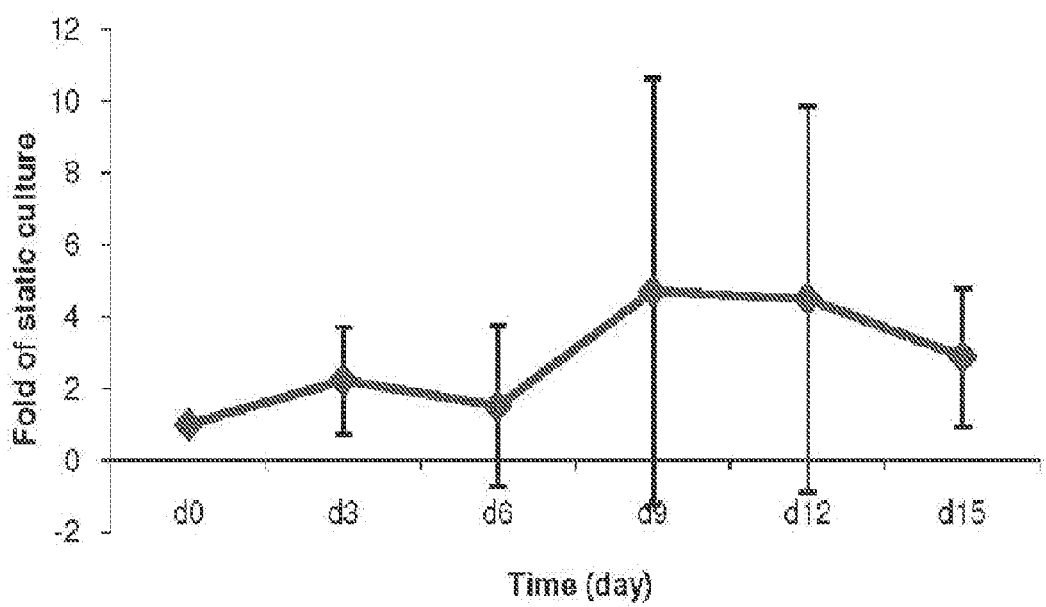
Figure 10G:
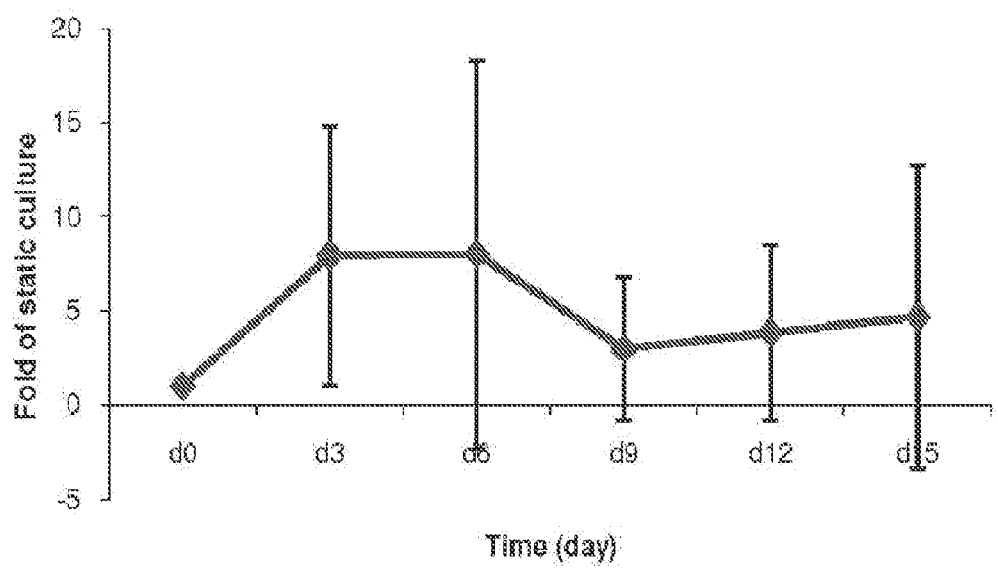
Figure 10H:
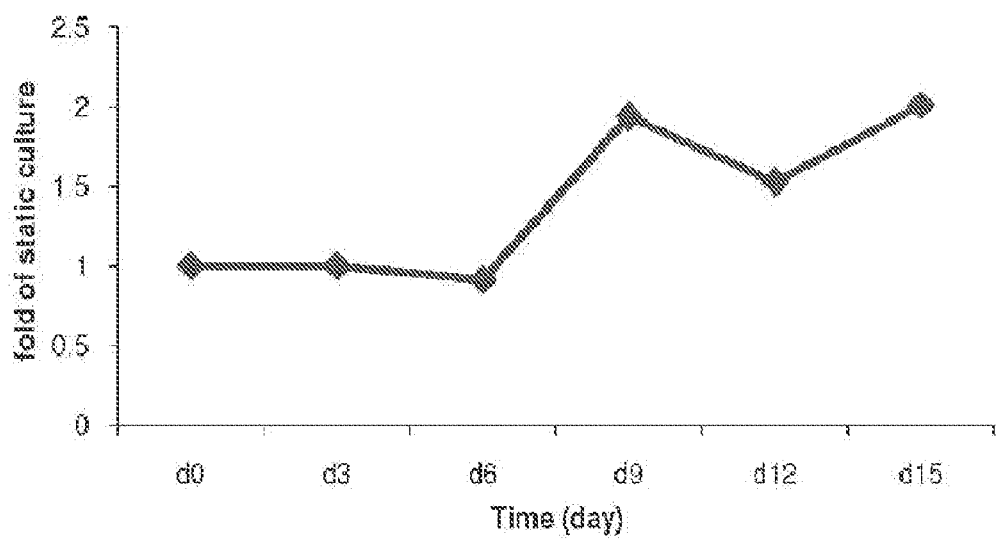

Differentiation of hESCs can be initiated by the formation of embryoid bodies (EBs) in suspension. Undifferentiated L-1 cells were removed from the maintenance culture by collagenase and shearing to clusters of approximately 100 cells. Directed differentiation was achieved through suspension culture in two different systems, 10 mL ultralow-attachment dishes (Corning) for static suspension culture and 100 mL bioreactor chambers (Wheaton) for stirred suspension cultures. The cells were inoculated at same density ($5.3 \times 10^5$ cells/ml) on day 0 in parallel cultures. Samples of EBs were collected at several time points to compare growth and differentiation parameters. The observation of EB morphology by phase contrast microscopy showed fewer aggregates of EBs in the bioreactor cultures than static cultures (FIG. 9a). Comparable cell numbers were obtained at the later stages of differentiation and similar viability levels were observed in the two differentiation conditions (FIG. 9b), which indicates that the EBs formed from iPS cells under 70 rpm stiffing in the bioreactor were not harmed by increased volume or shear forces from the apparatus. However, the data show that EB numbers decreased significantly after transferring the iPS colonies from maintenance culture (day 0) to directed differentiation (day 3) both in static and bioreactor cultures (FIG. 9c), possibly due to aggregation of individual EBs. Despite the similarity in EB numbers, aggregation of EBs in static culture appears to increase the average EB size over the bioreactor culture, especially midway through differentiation (day 9 in FIG. 9a) in this study. The observed difference in EB diameter between the static and bioreactor cultures was consistent with the observation of EB morphology by microscopy (FIGS. 9d, 9e and 9a). However, statistical analysis did not reveal a significant difference between the average EB size under the two culture conditions over the full differentiation course (p=0.0508). Thus, little or no aggregation was seen in the bioreactor cultures, and the EBs in static culture required manual dissociation when changing medium to protect the culture from forming too large aggregates to support cell survival. Total DNA and protein was measured in samples taken at each time point (FIGS. 9f, 9g) indicating higher concentrations in static culture than bioreactor during the early stages of differentiation (from day 0 to day 15), and similar concentrations during later stages (from day 15 to day 21), which is consistent with the cell number detection. These observations showed iPS cell differentiation cultures could be amplified simply from small static conditions to stirred large-scale bioreactors, which can provide large scale differentiated cells for clinic transplantation. Homogenous nutrient and gas perfusion in bioreactors can provide better conditions at later stages of differentiation. Stirred bioreactors provide uniform nutrient supply, including added cytokines, $O_2$ and $CO_2$ perfusion, and pH levels in cultured cells.

Bioreactor Culture Enhanced iPS Cell Differentiation into Pancreatic Progenitor Cells.

Bioreactor culture of iPS cell differentiation demonstrated comparable EB growth when compared with static cultures. In order to address whether the differentiation to pancreatic cells in the large-scale bioreactor culture was efficient, differentiation was measured by expression of specific pancreatic developmental markers, including definitive endoderm markers Foxa2 and Sox17; as well as pancreatic endoderm marker Pdx-1. Compared with the static culture, the results for bioreactor differentiation demonstrated the same pattern of development of pancreatic progenitor cells, which mimics in vivo pancreatic development (FIG. 10). Bioreactor cultures expressed higher levels of Pdx-1, which represents the differentiation of pancreatic progenitor cells. Published reports indicate that the transplantation of pancreatic progenitor cells reversed diabetes in mice efficiently. Since the differentiation of iPS cells in stirred bioreactor culture generated large numbers of cells with characteristics of pancreatic progenitors (FIG. 10b), the transplantation of iPS-derived cells from both conditions into diabetic mice were compared to determine their ability to regulate glucose in vivo.

Bioreactor Cultured iPS Derived Cells Enhanced Diabetic Mice Survival in Vivo.

Figure 11A:
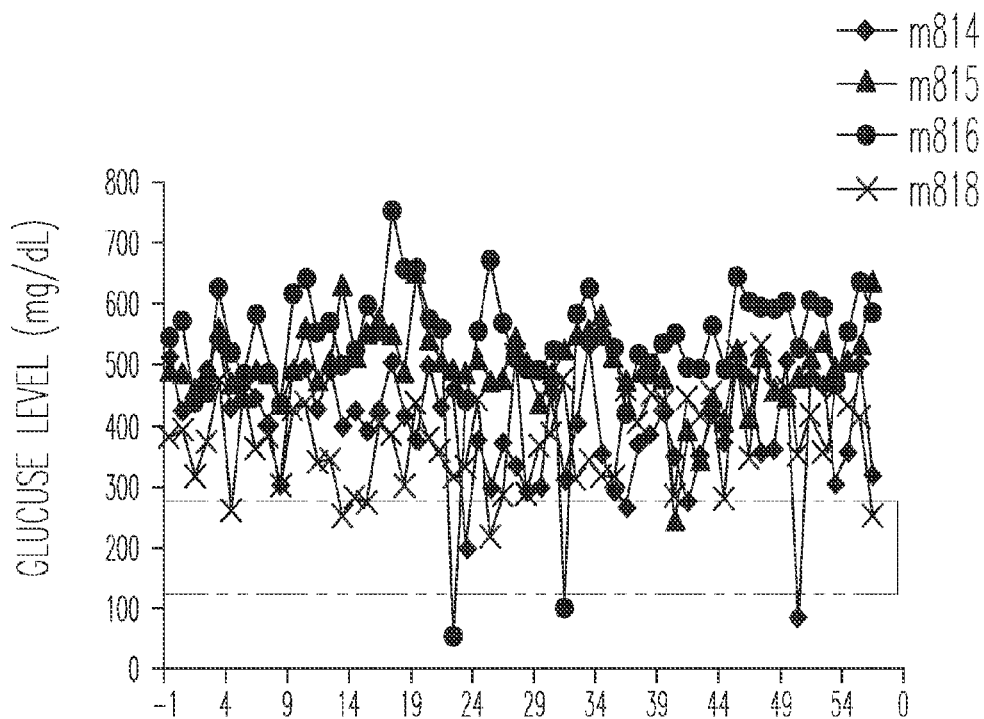
FIGS. 11A-C: Human iPS cells differentiated in stirred bioreactor cultures reversed diabetes in mice. (a) Day 15 differentiated iPS cultures from 10 ml static culture (group 1) were placed under the kidney capsule and (b) day 15 differentiated iPS culture from 100 ml stirred bioreactor culture (group 2&3) were placed in kidney capsule or the epididymal fat pad (EFP) of diabetic nude mice. Non-fasting blood glucose levels were monitored daily. The shaded area shows the average blood glucose level +/− two standard derivations form non-diabetic nude mice. (c) Comparison of average glucose levels for each mouse after transplantation, 10 ml static cells transplanted mice required insulin administration throughout the post-transplant period. Mice transplanted with 100 ml stirred bioreactor cells demonstrated a decrease in blood glucose levels controlled by the engrafted cells. The line indicated the survival glucose level (350 µg/ml).
Figure 11B:
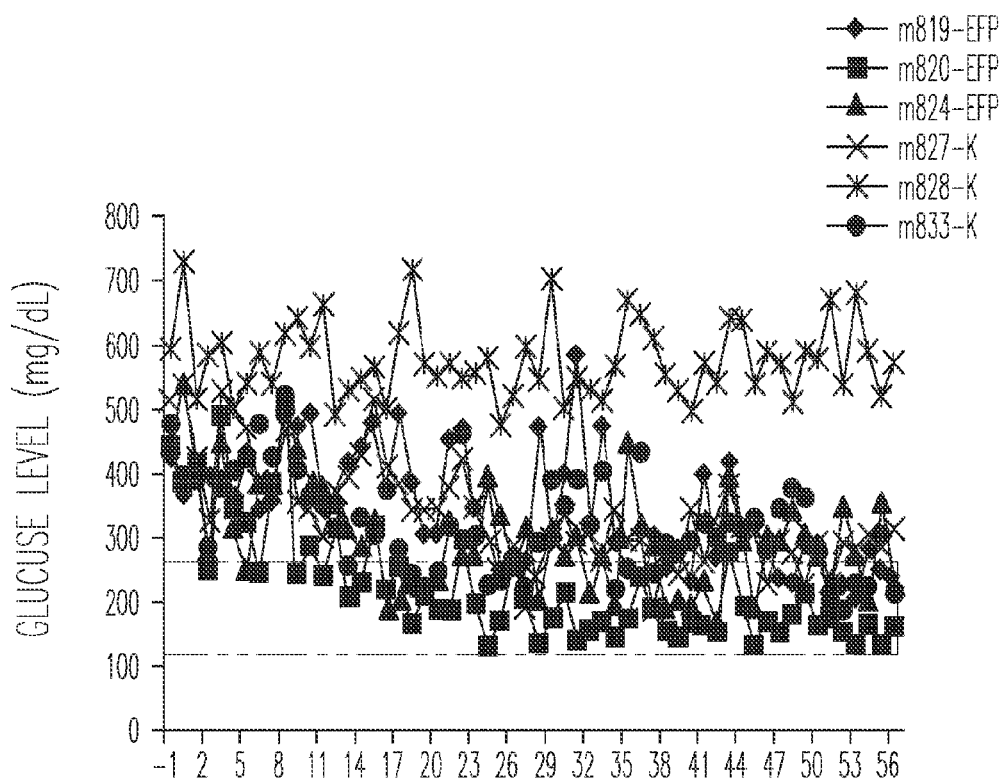
Figure 11C:
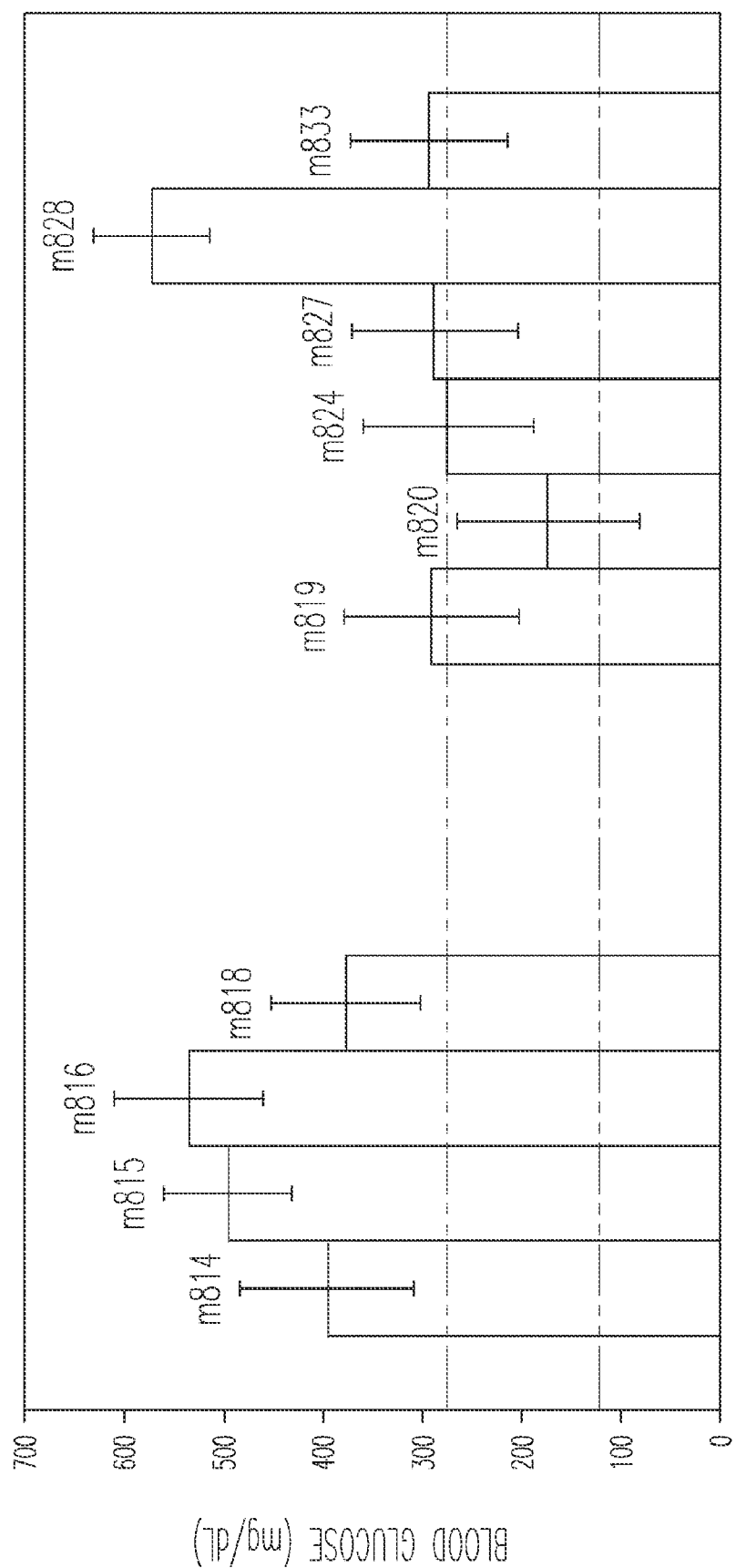

In a transplantation study, the timing of differentiation of iPS cells was optimized for transplantation into mice made diabetic by the injection of the beta cell toxin streptozoticin (STZ) using small-scale static cultures. Blood glucose levels and body weights were measured daily over a three week period without insulin administration after transplantation. Mice transplanted with day 15 static cultured cells showed a transient decrease in blood glucose levels. This suggested that the transplanted graft helped regulate glucose, because the levels observed were consistent with diabetic mice receiving insulin administration. Therefore, in the second phase of transplantation study, day 15 iPS-derived cells from both 10 ml static culture and 100 ml stirred bioreactor were transplanted to diabetic mice. Mice transplanted with cells from static cultures reduced blood glucose to levels that supported maintenance of body weight and survival (FIG. 11a and data not shown). In contrast, mice transplanted with cells from stirred bioreactors reduced blood glucose levels to normoglycemia in five of six mice tested (FIG. 11b).

Furthermore, in the same study, inoculated cell densities were compared for static and stirred cultured, to determine whether stirred bioreactors supported both higher cell volumes as well as higher density without loss of function in vivo. Three groups of differentiation cultures were set up: group 1, 10 ml static culture (at high density of about $1.4 \times 10^6$/ml); group 2, 100 ml stirred bioreactor culture at high density (about $1.4 \times 10^6$/ml); group 3, 100 ml stirred bioreactor culture at low density (about $7 \times 10^5$/ml). The culture and transplantation strategies are summarized in Table 3. Mice were maintained after transplantation with insulin administration until glucose was measured to be lower than 350 mg/dL, which is consistent with long-term survival. Blood glucose levels in mice after transplantation (FIG. 11b) show that bioreactor-cultured cells reversed diabetes in transplanted mice after a period of adaptation in vivo for over 3 weeks. Conversely, no mice transplanted with static-cultured cells showed sustained glucose levels below the target of 350 mg/dL during the post-transplant period. Therefore, differentiated cells from stirred bioreactors provided higher volume cultures and supported higher cell densities; and high yield and quality of cells that can be generated in bioreactors were effective for reversing diabetes in mice.

TABLE 3 iPS-derived cell transplantation summary

| Group | Mouse | Cells transplanted | Transplanted site |
|---|---|---|---|
| Group 1 | 814 | $2.6 \times 10^6$ | Kidney capsule |
| 10 ml static | 815 | $3.35 \times 10^6$ | Kidney capsule |
| high density | 816 | $2.7 \times 10^6$ | Kidney capsule |
|  | 818 | $2.25 \times 10^6$ | Kidney capsule |
| Group 2 | 828 | $5.5 \times 10^6$ | Kidney capsule |
| 100 ml bioreactor | 833 | $4.05 \times 10^6$ | Kidney capsule |
| high density | 820 | $8.2 \times 10^6$ | EFP |
|  | 824 | $5.85 \times 10^6$ | EFP |
| Group 3 | 827 | $3.45 \times 10^6$ | Kidney capsule |
| 100 ml bioreactor | 819 | $4.1 \times 10^6$ | EFP |
| low density |  |  |  |

Discussion

Pluripotent stem cells are actively being explored for replacement of damaged tissues in many cell types. Although many cell types, such as neural, muscle, hematopoietic, bone and pancreas have been generated from human pluripotent stem cells, clinical applications have lagged behind in vitro studies, partly because of the limitation of large-scale production of functional cells. Multiple mammalian cell lines such as HEK 293, CHO, Hela, NSO, vero cells have been cultured in bioreactors for producing recombinant proteins for clinic use. In industrial applications, there are mainly two types of stirred large scale culture methods. The first is a suspension culture in which cells grow in the medium and a stirring mechanism drives the cells to keep them in suspension. The other option is an anchorage dependent culture in which cells can either attach to the wall of the bioreactor, or attach to a microcarrier bead, which is then suspended in the medium in a stirred bioreactor. Each of these methods has their advantages and disadvantages, based on the cell line being used, as well as the production and scale. For clusters of cells such as EBs, the stirred bioreactor can be used, since beads are not required. Stirred suspension bioreactor culture systems offer the regulation of multiple parameters, including $O_2$ and $CO_2$ tension, cytokine, glucose and serum concentrations, as well as medium exchange rates, which may affect the viability and differentiation of stem cells into specific target cells. On the other hand, conventional stirrers may have the disadvantage of generating shear forces, which can damage cells, like the early stage cells indicated in this study. Using a slow stiffing speed of 70 rpm, this study demonstrated that cell numbers and viability in stirred bioreactor cultures is comparable with static cultures. Further, static cultures generated large clusters of EBs, which ultimately could impact gas and nutrient perfusion, causing cell necrosis.

Most of the previous published protocols for the differentiation of human pluripotent stem cells into pancreatic cells use several basal medium switches during the differentiation, and multiple cytokines are used to stimulate differentiation. Many of these protocols switch the culture from attachment at early stages to suspension cultures at later stages, complicating scale-up and, increasing costs. Since therapeutic applications require GMP manufacturing processes, reducing the number of added factors would facilitate clinical adaptation. In this study, we used only 3 cytokines, Activin A, Wnt3a and EGF and 1 monoclonal antibody, Anti-Shh before the cells were harvested for transplantation. Moreover, differentiation of iPS cells in this study was conducted with EBs (when cultured in suspension without antidifferentiation factors, some cells, such as stem cells, form three-dimensional multicellular aggregates called embryoid bodies (EBs)) throughout differentiation, which made scale up in stirred bioreactors easier.

The use of stirred bioreactors allowed the production of sufficient quantities of pancreatic progenitors to regulate glucose in vivo, without the loss of viability or reduction in growth rates. While the in vitro analysis suggested that the products of the static and stirred bioreactor cultures were similar, the results in vivo indicate that only the cells from large-scale culture promoted normoglycemia in mice. In summary, this study is the first to demonstrate that human iPS cells can be differentiated in large-scale cultures to pancreatic progenitor cells that can reverse diabetes.

Bibliopgraphy

Cabrita G J M, et al. *TRENDS in Biotechnology* Vol. 21 No. 5 May 2003.

Chu L and Robinson D K. *Current Opinion in Biotechnology* 2001, 12:180-187.

D'Amour K A, et al. *Nature Biotechnol.* 2006; 24:1392-1401.

Fridley K M, et al. *TISSUE ENGINEERING:* Part A Vol 00, No 00, 2010.

Gerecht-Nir S, et al. *Biotechnology and Bioengineering*, vol. 86(5), 2004

Jiang W, et al. *Cell Res.* 2007; 17:333-344.

Krawetz R, et al. *TISSUE ENGINEERING: Part C Vol* 00, No 00, 2009.

Kroon E, et al. *Nat. Biotechnol.* 2008; 26:443-452.

Liew, C G. *Rev Diabet Stud,* 2010, 7(2):82-92.

Maehr R, et al. *Proc. Natl. Acad. Sci. U.S.A.* 2009; 106: 15768-15773.

Phillips B W, et al. *Stem Cells Dev.* 2007; 16:561-578.

Schroeder M, et al. *Biotechnology and Bioengineering*, vol. 92(7), 2005.

Sen A, et al. *Biotechnol. Prog.* 2002, 18, 337-345.

Shim J H, et al. *Diabetologia* 2007; 50:1228-1238.

Takahashi K, et al. *Cell* 2007; 131:861-872.

Takahashi K and Yamanaka S. *Cell* 2006; 126:663-676.

Tateishi K, et al. *J. Biol. Chem.* 2008; 283:31601-31607.

Yirme G, et al. *Stem Cells and Development* 17:1227-1242 (2008).

Yu J, et al. *Science* 2007; 318:1917-1920.

Zhang D W, et al. *Cell Res.* 2009; 19:429-438.

Evans M J and Kaufman M H. *Nature* 292, 154-156 (1981).

Martin G R. *PNAS.* 78, 7634-7638 (1981).

Thomson J A, et al. *Science* 282, 1145-1147 (1998).

Keller, G. et al. *Gene & Dev.* 19, 1129-1155 (2005).

Soria B, et al. *Diabetologia* 44, 407-415 (2001).

Kumar M and Melton D. *Curr Opin Genet. Dev.* 13, 401-407 (2003).

Magliocca and Odorico. *Curr Opin Organ Transplant* 11, 88-93 (2006)

Madsen, O. D. *APMIS.* 113, 858-875 (2006).

D'Amour, K. A. et al. *Nat. Biotechnol.* 23, 1534-1541 (2005).

Habener J. F., et al. *Endocrinology* 146, 1025-1034 (2005).

Jensen J. *Dev Dyn.* 229, 176-200 (2004).

Shi, Y. et al. *Stem Cells* 23, 656-662 (2005).

The complete disclosure of all patents, patent documents and publications cited herein are incorporated herein by reference as if individually incorporated. The foregoing detailed description and examples have been given for clarity of understanding only. No unnecessary limitations are to be understood therefrom. The invention is not limited to the exact details shown and described for variations obvious to one skilled in the art will be included within the invention defined by the claims.

---

What we claim is:

1. An in vitro method to differentiate stem cells to pancreatic progenitor cells comprising the steps of:
   a) contacting the stem cells with at least one member of the TGFβ family of cytokines and at least one member of the Wnt family of proteins,
   b) contacting the cells obtained from step a) with at least one member of the TGFβ family of cytokines, at least one member of the Wnt family of proteins, and an agent that inhibits sonic hedgehog activity; and
   c) contacting the cells obtained from step b) with a member of the Epidermal growth factor (EGF) family of proteins;
   so as to yield pancreatic progenitor cells.

2. The method of claim 1, wherein the at least one member of the TGFβ family of cytokines is activinA or nodal.

3. The method of claim 1, wherein the at least one member of the Wnt family is Wnt 3 or Wnt 3A.

4. The method of claim 1, wherein the at least one member of the EGF family is EGF.

5. The method of claim 1, wherein the stem cells are embryonic or adult stem cells.

6. The method of claim 1, wherein the stem cells are induced pluripotent stem (iPS) cells.

7. The method of claim 1 further comprising contacting the cells obtained from step c) with at least one member of the TGFβ family of cytokines, betacellulin, exendin4 or a combination thereof to yield cells expressing insulin.

8. The method of claim 7, wherein the at least one member of the TGFβ family of cytokines is GDF-11.

9. The method of claim 7, wherein the cells expressing insulin or having increased expression of insulin secrete insulin, c-peptide or a combination thereof.

10. The method of claim 7, wherein the insulin is insulin-1.

11. The method of claim 1, wherein the agent that inhibits sonic hedgehog activity is cyclopamine or an anti-SHH antibody.

12. The method of claim 1, wherein the stem cells are mammalian cells.

13. The method of claim 12, wherein the mammalian cells are human cells.

14. The method of claim 1, wherein the differentiation occurs in a cell culture dish.

15. The method of claim 1, wherein the differentiation occurs in bioreactor.

16. An in vitro method to differentiate stem cells to pancreatic progenitor cells comprising the steps of:
   a) contacting the stem cells with Activin A and Wnt3 a,
   b) contacting the cells obtained from step a) with Activin-A, Wnt3 a, and an agent that inhibits sonic hedgehog activity; and
   c) contacting the cells obtained from step b) with EGF;
   so as to yield pancreatic progenitor cells.

* * * * *

SEQUENCE LISTING

```
<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: A synthetic primer

<400> SEQUENCE: 1
gagtcaacgg atttggtcgt                                              20

<210> SEQ ID NO 2
<211> LENGTH: 20
<212> TYPE: DNA
<213> ORGANISM: Artificial Sequence
<220> FEATURE:
```

```
<223> OTHER INFORMATION: A synthetic primer

<400> SEQUENCE: 2
gacaagcttc ccgttctcag                                               20

<210> SEQ ID NO 3
<211> LENGTH: 20
<212> TYPE: DNA
<213> ORGANISM: Artificial Sequence
<220> FEATURE:
<223> OTHER INFORMATION: A synthetic primer

<400> SEQUENCE: 3
cgcacggaat ttgaacagta                                               20

<210> SEQ ID NO 4
<211> LENGTH: 20
<212> TYPE: DNA
<213> ORGANISM: Artificial Sequence
<220> FEATURE:
<223> OTHER INFORMATION: A synthetic primer

<400> SEQUENCE: 4
ggatcaggga cctgtcacac                                               20

<210> SEQ ID NO 5
<211> LENGTH: 20
<212> TYPE: DNA
<213> ORGANISM: Artificial Sequence
<220> FEATURE:
<223> OTHER INFORMATION: A synthetic primer

<400> SEQUENCE: 5
attgctggtc gtttgttgtg                                               20

<210> SEQ ID NO 6
<211> LENGTH: 20
<212> TYPE: DNA
<213> ORGANISM: Artificial Sequence
<220> FEATURE:
<223> OTHER INFORMATION: A synthetic primer

<400> SEQUENCE: 6
tacgtgttca tgccgttcat                                               20

<210> SEQ ID NO 7
<211> LENGTH: 22
<212> TYPE: DNA
<213> ORGANISM: Artificial Sequence
<220> FEATURE:
<223> OTHER INFORMATION: A synthetic primer

<400> SEQUENCE: 7
cattggaagg ctccctaaca ca                                            22

<210> SEQ ID NO 8
<211> LENGTH: 20
<212> TYPE: DNA
<213> ORGANISM: Artificial Sequence
<220> FEATURE:
<223> OTHER INFORMATION: A synthetic primer

<400> SEQUENCE: 8
ggcatcaatt tcacgggatc                                               20
```

<210> SEQ ID NO 9
<211> LENGTH: 20
<212> TYPE: DNA
<213> ORGANISM: Artificial Sequence
<220> FEATURE:
<223> OTHER INFORMATION: A synthetic primer

<400> SEQUENCE: 9
ctacctagtg tgcggggaac                                              20

<210> SEQ ID NO 10
<211> LENGTH: 20
<212> TYPE: DNA
<213> ORGANISM: Artificial Sequence
<220> FEATURE:
<223> OTHER INFORMATION: A synthetic primer

<400> SEQUENCE: 10
gctggtagag ggagcagatg                                              20

<210> SEQ ID NO 11
<211> LENGTH: 39
<212> TYPE: PRT
<213> ORGANISM: Homo sapiens

<400> SEQUENCE: 11

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 12
<211> LENGTH: 43
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 2-8, 10-14, 16-28, 30, 32-39, 41
<223> OTHER INFORMATION: Xaa = any amino acid

<400> SEQUENCE: 12

Cys Xaa Xaa Xaa Xaa Xaa Xaa Xaa Cys Xaa Xaa Xaa Xaa Xaa Cys Xaa
 1               5                  10                  15

Xaa Xaa Xaa Xaa Xaa Xaa Xaa Xaa Xaa Xaa Xaa Xaa Cys Xaa Cys Xaa
            20                  25                  30

Xaa Xaa Xaa Xaa Xaa Xaa Xaa Gly Xaa Arg Cys
        35                  40

<210> SEQ ID NO 13
<211> LENGTH: 20
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 5-6, 8-9, 12-15, 17, 19
<223> OTHER INFORMATION: Xaa = any amino acid

```
<400> SEQUENCE: 13

Leu Ile Val Met Xaa Xaa Pro Xaa Xaa Phe Tyr Xaa Xaa Xaa Xaa Cys
1               5                   10                  15

Xaa Gly Xaa Cys
            20
```